US009072533B2

(12) United States Patent
Liu et al.

(10) Patent No.: US 9,072,533 B2
(45) Date of Patent: Jul. 7, 2015

(54) DERMATOLOGICAL TREATMENT DEVICE WITH ONE OR MORE MULTI-EMITTER LASER DIODE

(75) Inventors: Harvey I-Heng Liu, Fremont, CA (US); Patrick Reichert, Dublin, CA (US)

(73) Assignee: TRIA BEAUTY, INC., Dublin, CA (US)

( * ) Notice: Subject to any disclaimer, the term of this patent is extended or adjusted under 35 U.S.C. 154(b) by 65 days.

(21) Appl. No.: 13/425,995

(22) Filed: Mar. 21, 2012

(65) Prior Publication Data

US 2012/0253334 A1 Oct. 4, 2012

Related U.S. Application Data

(60) Provisional application No. 61/469,316, filed on Mar. 30, 2011, provisional application No. 61/533,641, filed on Sep. 12, 2011, provisional application No. 61/533,677, filed on Sep. 12, 2011, provisional application No. 61/533,786, filed on Sep. 12, 2011, provisional application No. 61/545,481, filed on Oct. 10, 2011, provisional application No. 61/594,128, filed on Feb. 2, 2012.

(51) Int. Cl.
*A61B 5/06* (2006.01)
*A61B 18/20* (2006.01)

(52) U.S. Cl.
CPC .................................... *A61B 18/203* (2013.01)

(58) Field of Classification Search
CPC ................ A61B 18/20; A61B 18/203; A61B 18/00452; A61B 2018/00636
USPC ................ 606/2, 10, 11; 607/88, 89; 128/898
See application file for complete search history.

(56) References Cited

U.S. PATENT DOCUMENTS

| 5,541,949 A * | 7/1996 | Bhat et al. ................ 372/45.011 |
| 7,763,016 B2 | 7/2010 | Altshuler et al. .................. 606/9 |
| 2004/0152943 A1 | 8/2004 | Zimmerman et al. .......... 600/13 |

(Continued)

FOREIGN PATENT DOCUMENTS

| EP | 1146617 A2 | 10/2001 | ............. A61B 18/20 |
| GB | 2381752 A | 5/2003 | ............. A61B 18/20 |

OTHER PUBLICATIONS

"What Limits the Outpu Power of Long-Wavelength AlGaInAs/InP Laser Diodes" Piprek et al. IEEE Journal of Quantum Electronics, vol. 38, No. 9, Sep. 2002.*

(Continued)

*Primary Examiner* — Aaron Roane
(74) *Attorney, Agent, or Firm* — King & Spalding L.L.P.

(57) ABSTRACT

A dermatological treatment device includes a handheld device body, and a laser control circuit housed in the device body and configured to generate laser radiation for delivery to a target area of tissue. The laser control circuit includes a multiple-emitter laser diode and a battery source. The multiple-emitter laser diode includes a monolithic stack of layers formed on a substrate, the monolithic stack of layers including a multiple-emitter region defining at least two emitter junctions, each emitter junction configured to emit a laser beam. The battery source provides current to the laser diode such that each of the at least two emitter junctions concurrently emits a laser beam, the at least two concurrently emitted laser beams forming a collective beam. The device delivers the collective beam to the target area of tissue to provide a dermatological treatment.

29 Claims, 13 Drawing Sheets

(56) References Cited

U.S. PATENT DOCUMENTS

| 2006/0004306 | A1 | 1/2006 | Altshuler et al. ............. 601/3 |
| 2007/0032847 | A1 | 2/2007 | Weckwerth et al. ........... 607/93 |
| 2008/0015556 | A1 | 1/2008 | Chan et al. .................... 606/9 |
| 2008/0058783 | A1* | 3/2008 | Altshuler et al. .............. 606/9 |
| 2008/0077198 | A1 | 3/2008 | Webb et al. ................... 607/88 |
| 2009/0069741 | A1 | 3/2009 | Altshuler et al. .............. 604/22 |
| 2012/0253334 | A1 | 10/2012 | Liu et al. ....................... 606/9 |

OTHER PUBLICATIONS

Technical specification for Giga GD20483 laser diode, 1999.*
Technical specification for JDS Uniphase RL30 series, 2001.*
Giga GD20483 laser diode (tech specs 1999).*
JDS Uniphase RL30 series (tech specs 2001).*
Technical specs of the Giga Corporation's laser diode GD20483, 3rd revision data sheet, published Nov. 12, 1999. Already in record.*
Ikoma, N. et al., "Highly Reliable AlGaInAs Buried Heterostructure Lasers for Uncooled 10Gb/s Direct Modulation," Optical Fiber Communications Conference Technical Digest, IEEE, XP010831967, 3 pages, Mar. 6, 2005.
Paschotta, Rüdiger, "Diode Bars," Encyclopedia of Laser Physics and Technology, RP Photonics Consulting GmbH, www.rp-photonics.com/diode_bars.html, 7 pages, May 27, 2011.
International Search Report and Written Opinion, Application No. PCT/US2012/066261, 10 pages, Feb. 19, 2013.
International Search Report and Written Opinion, Application No. PCT/US2013/024287, 13 pages, Apr. 26, 2013.

* cited by examiner

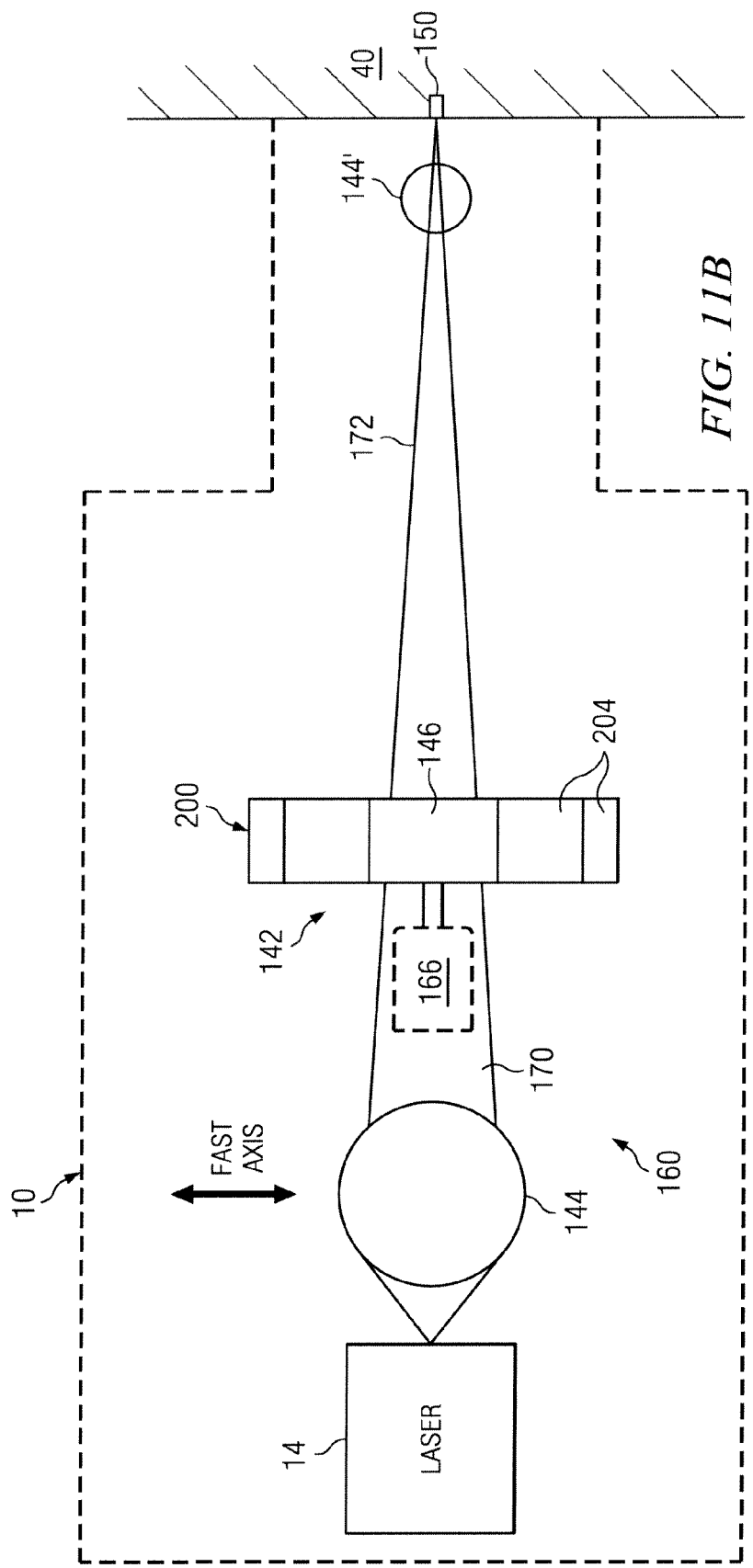

DERMATOLOGICAL TREATMENT DEVICE WITH ONE OR MORE MULTI-EMITTER LASER DIODE

CROSS-REFERENCE TO RELATED APPLICATIONS

This application claims the benefit of U.S. Provisional Application No. 61/469,316 filed on Mar. 30, 2011; U.S. Provisional Application No. 61/533,641 filed on Sep. 12, 2011; U.S. Provisional Application No. 61/533,677 filed on Sep. 12, 2011; U.S. Provisional Application No. 61/533,786 filed on Sep. 12, 2011; U.S. Provisional Application No. 61/545,481 filed on Oct. 10, 2011; U.S. Provisional Application No. 61/594,128 filed on Feb. 2, 2012; all of which disclosures are herein incorporated by reference in their entirety.

TECHNICAL FIELD

The present disclosure is related to laser diodes and systems that incorporate laser diodes, an in particular to integral or monolithic multi-emitter laser diodes, e.g., for use in dermatological treatment devices.

BACKGROUND

Laser-based treatment of tissue is used for a variety of applications, such as hair removal, skin rejuvenation, wrinkle treatment, acne treatment, treatment of vascular lesions (e.g., spider veins, diffuse redness, etc.), treatment of cellulite, treatment of pigmented legions (e.g., age spots, sun spots, moles, etc.), tattoo removal, and various other treatments. Such treatments generally include delivering laser radiation to an area of tissue on a person's body, e.g., the skin or internal tissue, to treat the tissue in a photochemical, photobiological, thermal, or, other manner, which can be ablative or non-ablative, among other properties, depending on the particular application.

Laser-based treatment devices may include any suitable type of laser, e.g., laser diode, fiber laser, VCSEL (Vertical Cavity Surface Emitting Laser), LED, etc.

A device may include a single laser or multiple lasers, e.g., a laser diode bar including multiple distinct emitters arranged in a row, or multiple fiber lasers arranged in a row or array.

Laser diodes are particularly suitable for certain laser-based treatments and devices for providing such treatments. For example, laser diodes are compact, as they are typically built on one chip that contains all necessary components. Further, laser diodes typically provide an efficiency of up to 50%, which enables them to be driven by low electrical power compared to certain other lasers. Further, laser diodes allow direct excitation with small electric currents, such that conventional transistor based circuits can be used to power the laser.

Other characteristics of laser diodes include high temperature sensitivity/tunability, and a highly divergent beam compared to certain other lasers. Laser diodes typically emit a beam having an axis-asymmetric profile in a plane transverse to the optical axis of the laser. In particular, the emitted beam diverges significantly faster in a first axis (referred to as the "fast axis") than in an orthogonal second axis (referred to as the "slow axis"). In contrast, other types of lasers, e.g., fiber lasers, typically emit a beam having a axis-symmetric profile in the transverse plane.

Laser-baser treatment devices include larger-scale devices typically operated by a physician or other professional in a clinic or other office, as well as hand-held devices for home-use, allowing users to provide treatment to themselves. Some hand-held laser-baser treatment devices are battery powered, e.g., using a Li ion battery cell (or multiple cells). Such battery-powered devices may be recharged between use, e.g., by plugging into an A/C wall outlet, either directly or by docking in a docking unit plugged into the wall.

Some laser-baser treatment devices apply laser radiation directly from the laser source to the target tissue to create a pattern of radiated areas (e.g., spots, lines, or other shapes) in the tissue. Others include optics between the laser source and the target tissue. Such optics may include optical elements such as lenses, mirrors, and other reflective and/or transmissive elements, for controlling optical parameters of the beam, such as the direction, shape (e.g., convergent, divergent, collimated), spot size, angular distribution, temporal and spatial coherence, and/or intensity profile of the beam. Some devices include systems for scanning a laser beam in order to create a pattern of radiated areas (e.g., spots, lines, or other shapes) in the tissue. For some applications, the scanned pattern of radiated areas overlap each other, or substantially abut each other, or are continuous, in order to provide generally complete coverage of a target area of tissue. For other applications, e.g., certain wrinkle treatments and other skin rejuvenation treatments, the scanned radiated areas may be spaced apart from each other such that only a fraction of the overall target area of the tissue is radiated. In this case, there are generally regions of untreated tissue between regions of treated tissue. This latter type of treatment is known as "fractional" treatment (or more specifically, fractional photothermolysis) because only a fraction of the target area is irradiated.

Laser-baser treatment devices may deliver radiation as continuous wave (CW) radiation, pulsed radiation, or in any other manner, and according to any suitable parameters, e.g., wavelength, current, power level, etc. For example, wavelengths absorbed by water in the skin, e.g., between 1400 and 2000 nm, may be used for certain laser-based treatments. For certain "fractional" non-ablative skin treatments, a wavelength of about 1450-1550 nm±50 nm may be used, with a total energy of about 2 mJ-30 mJ delivered to the target tissue at each treatment spot, or "microthermal zone" (MTZ).

SUMMARY

In some embodiments of the present disclosure, a dermatological treatment device includes a handheld device body, and a laser control circuit housed in the device body and configured to generate laser radiation for delivery to a target area of tissue. The laser control circuit includes a multiple-emitter laser diode and a battery source. The multiple-emitter laser diode includes a monolithic stack of layers formed on a substrate, the monolithic stack of layers including a multiple-emitter region defining at least two emitter junctions, each emitter junction configured to emit a laser beam. The battery source provides current to the laser diode such that each of the at least two emitter junctions concurrently emits a laser beam, the at least two concurrently emitted laser beams forming a collective beam. The device delivers the collective beam to the target area of tissue to provide a dermatological treatment.

In some embodiments of the present disclosure, a method for providing a dermatological treatment includes providing a handheld device including a laser control circuit comprising (a) a multiple-emitter laser diode including a monolithic stack of layers formed on a substrate, the monolithic stack of layers including a multiple-emitter region defining at least two emitter junctions, each emitter junction configured to emit a laser beam, and (b) a battery source. Current is provided via the laser control circuit from the battery source to the laser diode to cause each of the at least two emitter junctions to concurrently emit a laser beam, the at least two concurrently emitted laser beams forming a collective beam. The collective beam is then delivered to the target area of tissue to provide a dermatological treatment.

BRIEF DESCRIPTION OF THE DRAWINGS

Some embodiments of the disclosure may be understood by referring, in part, to the following description and the accompanying drawings wherein:

FIGS. 11A and 11B illustrate top and side views, respectively, of a beam delivery system that includes a rotating scanning element, according to certain embodiments.

FIG. 12 illustrates an example pattern of treatment spots delivered by one scan of a light beam by scanning system, in a stationary mode of the device.

DETAILED DESCRIPTION OF THE DRAWINGS

Figure 1:
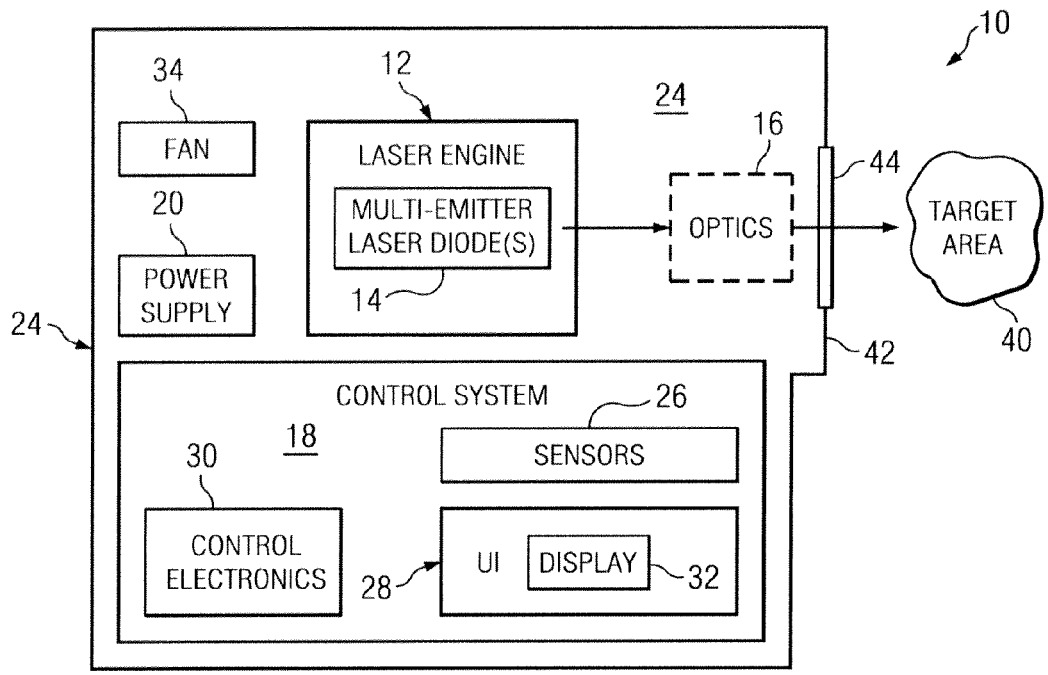
FIG. 1 illustrates components of an example laser-based treatment device including one or more multi-emitter laser diodes, according to certain embodiments

Some embodiments of the disclosure may be understood by referring, in part, to the following description and the accompanying drawings, in which like reference numbers refer to the same or like parts.

Certain aspects of the present disclosure are related to dermatological treatment devices that incorporate at least one multi-emitter laser diode. As used herein, the term "multi-emitter laser diode" refers to an integral or monolithic edge-emitting laser diode structure having multiple emitter junctions formed on a substrate, such as a "multiple quantum well" (MQW) laser diode, for example. Some multi-emitter laser diode include an integrated or monolithic stack of layers formed on a single substrate, the monolithic stack of layers including a multiple-emitter region defining at least two emitter junctions, each emitter junction configured to emit an individual laser beam. A multi-emitter laser diode having exactly two emitter junctions is referred to herein as a "dual-emitter laser diode." The individual laser beams of the multiple emitters of a multi-emitter laser diode may at least partially combine or interact, such that the combined radiation of the multiple emitters is referred to herein as a "collective beam."

The term "multi-emitter laser diode" is distinguished from (a) a collection of single-emitter laser diodes arranged together and/or physically connected, e.g., a laser diode bar having multiple single-emitter laser diodes arranged in a row, and (b) "surface emitting" lasers, e.g., VCSELs (Vertical Cavity Surface Emitting Lasers). However, multiple multi-emitter laser diodes may be arranged as a laser bar or otherwise arranged together and/or physically connected, e.g., to provide a one-dimensional or two-dimensional array of laser diodes. Thus, certain embodiments of devices according to the present disclosure include multiple multi-emitter laser diodes, e.g., arranged as a laser diode bar, arranged in a one-dimensional or two-dimensional array, or otherwise arranged.

Multi-emitter laser diodes may provide one or more advantages in the context of dermatological treatment devices, e.g., as compared to single-emitter laser diodes. For example, multi-emitter laser diodes may increase the laser engine system efficiency of battery-powered laser treatment devices (e.g., devices using one or more Li-ion or other batteries), as compared to similar devices using single-emitter laser diodes. For instance, a multi-emitter laser diode may provide an intrinsic voltage drop that more closely matches the battery source cell voltage with better optical system efficiency operating at a lower drive current, as compared with a single-emitter laser diode, as explained below.

The laser engine system efficiency is typically important to the performance of a battery operated laser treatment device. The more efficient the laser engine system, the longer the device can be operated between battery charges. Increased laser engine system efficiency may also allow treatment of larger areas and/or more treatment sessions in a single charge. To achieve increased efficiency performance, it may be desirable to closely match the voltage characteristics of the laser diode and the battery system. As mentioned above, a multi-emitter laser diode may provide an intrinsic voltage drop that more closely matches the battery voltage, as compared with a single-emitter laser diode, thus providing increased efficiency performance.

In a typical constant-current laser diode drive system, the electrical circuit consists of a battery source, a laser diode, a current control transistor, one or more switches, and other passive current sensing resistors, all connected in series. In an efficient design, a high percentage of the battery source voltage drops across the laser diode with minimal waste heat dissipation in the current control transistor. Thus, it may be desirable that the forward voltage drop of the laser diode approaches the battery voltage for the output optical power needed for the desired treatment application.

In the case of a Li ion battery cell, the cell voltage typically ranges from about 2.8 to 3.8 V, depending on the specific cell chemistry and the battery charge state. For a typical infrared laser diode used in non-ablative treatment with wavelength in the example range of 1400 nm to 1550 nm, the intrinsic forward diode voltage drop is less than 1.5 V. This is significantly below the Li cell voltage and thus results in excess waste heat at the current control transistor. Thus, it may be desirable to increase the intrinsic laser diode voltage drop and concurrently increase its optical output power to provide a more efficient system. This can be achieved by using multi-emitter laser diodes, in which the multiple emitter diode junctions are arranged in electrical series. For example, a dual-emitter laser diode can achieve a forward voltage drop close to or even above 2.5 V and thereby increase the laser optical output by about 60% for the same drive current level relative to a single-emitter laser diode. (e.g., as discussed below with respect to FIG. 5).

As discussed below, in a multi-emitter laser diode according to at least some embodiments, the multiple laser emitter junctions are integrated and monolithically grown onto a single substrate. The consecutive emitter junctions may be separated by several micrometers. The far-field beam angular distribution is similar to that of a typical single-emitter-junction case, as discussed below with reference to FIGS. 6A-6B). For "direct exposure" embodiments of device 10 (defined below), the target spot size and beam profile are largely indistinguishable from that of a typical single-emitter-junction device. However, for "indirect exposure" embodiments of device 10 (defined below), the beam profile in the fast-axis may define multiple spaced-apart peaks, corresponding to the multiple emitter junctions, which may result in a larger spot size in the fast-axis direction, as compared to that of a single-emitter-junction. Thus, additional focusing optics may be provided in certain indirect exposure embodiments to refocus the collective beam in the fast-axis direction, e.g., for applications in which a very small laser spot size is desired at the target surface, as discussed below with reference to FIGS. 7A-7B. In an example embodiment, this fast-axis refocusing can be achieved with a simple cylindrical rod lens positioned near the target surface, e.g., as discussed below with reference to FIGS. 8A-8D.

In some embodiments, multi-emitter laser diode(s) may be employed as the edge emitting laser diode(s) in any of the various embodiments and configurations, incorporating any of the various features, functionality, and operational aspects, and for providing any of the various treatments as disclosed in U.S. patent application Ser. No. 13/366,246 filed Feb. 3, 2012 (hereinafter, "U.S. Ser. No. 13/366,246") which disclosures is incorporated by reference in its entirety.

FIG. 1 illustrates components of an example laser-based treatment device 10, according to certain embodiments. Laser-based treatment device 10 may include a laser engine 12 including one or more multi-emitter laser diodes 14 configured to generate one or more laser beams, optics 16 for delivering the laser beam(s) to a target area 40 (e.g., an area of tissue), a control system 18, one or more power supplies 20, and one or more fans 34.

As discussed below, "direct exposure" embodiments may omit optics 16 such that no optics are provided between laser diode(s) 14 and the target surface, for direct exposure of the target tissue. In some direct exposure embodiments, laser diode(s) 14 are located in close proximity to the target skin surface (e.g., less than 10 mm, less than 2 mm, or less than 1 mm, less than 500 µm, less than 200 µm, or even less than 100 µm from the target skin surface).

The components of device 10 may be provided in a structure or housing 24, or alternatively may be provided in separate structures or housings and connected in any suitable manner, e.g., via fiber optic or other cabling. Housing 24 may define an application end 42 configured to be placed in contact with the target surface (e.g., skin) during treatment of the target area 40. Application end 42 may include or house various user interfaces, including the treatment delivery interface for delivering output beams 94 to the user, as well as one or more sensors 26 for detecting various characteristics of the target surface and/or treatment delivered by device 10. In some embodiments, application end 42 may include an aperture or window 44 through which the laser beam is delivered to the target surface, or alternatively, an optical element 16 (e.g., a lens) may be located at application end 42 and configured for direct contact or very close proximity with the skin during treatment.

Device 10 may include any other components suitable for providing any of the functionality discussed herein or other related functionality known to one of ordinary skill in the art.

Laser engine 12 may include one or more multi-emitter laser diodes 14. Where device 10 includes multiple multi-emitter laser diodes 14, the multiple laser diodes 14 may be arranged proximate each other and/or connected to each other (e.g., in a laser diode bar, one-dimensional array, or two-dimensional array arrangement), or may be spaced apart from each other.

The multi-emitter laser diode(s) 14 of device 10 may be configured for and/or operated at any suitable wavelength to provide the desired treatment. For example, multi-emitter laser diode(s) 14 may be configured for and/or operated at a wavelength that is absorbed by water in the skin, e.g., between 1400 nm and 2000 nm, e.g., for certain photothermolysis treatments. In some embodiments, multi-emitter laser diode(s) 14 may be configured for and/or operated at a wavelength of about 1450-1550 nm±50 nm, e.g., for certain fractional non-ablative skin treatments. In other embodiments, multi-emitter laser diode(s) 14 may be configured for and/or operated at a wavelength of between 650 nm and 1100 nm (e.g., about 810 in some applications), e.g., for hair removal treatment. In other embodiments, multi-emitter laser diode(s) 14 may be configured for and/or operated at a wavelength of between 1700 nm and 1800 nm, e.g., for sebatious gland related treatment like acne. In still other embodiments, multi-emitter laser diode(s) 14 may be configured for and/or operated at a wavelength of between 1900 nm and 1950 nm, e.g., for pigmented lesion treatment like solar lentigo.

Further, multi-emitter laser diode(s) 14 may be configured or operated to deliver continuous wave (CW) radiation, quasi-CW radiation, pulsed radiation, or in any other manner. In some embodiments, device 10 controls multi-emitter laser diode(s) 14 to provide CW radiation or quasi-CW radiation, e.g., for bulk heating skin tightening or hair removal. In other embodiments, device 10 controls multi-emitter laser diode(s) 14 to provide pulsed radiation, e.g., for selective photothermalysis. For example, in some embodiments, device 10 may be configured to sequentially deliver a series of laser beams (specifically, collective beams 94 discussed below) to the target area 40 to generate treatment spots that are spaced apart from each other by areas of non-irradiated skin between the adjacent treatment spots, to provide a "fractional" treatment, e.g., for skin rejuvenation, wrinkle treatment, or treatment of pigmented legions (e.g., age spots, sun spots, moles, etc.).

Certain embodiments of device 10 include one or more optics 16 downstream of laser diode 14 for directing or treating the beam 94 emitted from laser diode 14 before reaching the target surface. Optics 16 may allow for laser diode 14 to be positioned at any desired distance from the application end 42 of the device that contacts the skin during treatment (and thus at any desired distance from the target surface). Embodiments of device 10 that include optics 16 downstream of laser engine 12 are referred to herein as "indirect exposure" embodiments.

Optics 16 may include any number and types of optical elements for delivering the light generated by laser engine 12 to the target area 40 and, if desired, for treating the beam, such as adjusting the treatment spot size, intensity, spot location, angular distribution, coherence, etc. In some embodiments, optics 16 may include a scanning system for scanning a pattern of treatment spots on the target area 40, as discussed below. Beam treatment optics may be included before and/or after the scanning system or may be interspersed with the scanner or part of the scanning system.

As used herein, an "optic" or "optical element" may mean any element that deflects a light beam, influences the angular distribution profile (e.g., angle of convergence, divergence, or collimation) of a laser beam in at least one axis, influences the focus of the beam in at least one axis, or otherwise affects a property of the radiation. Thus, optics include mirrors and other reflective surfaces, lenses, prisms, light guides, gratings, filters, etc. For the purposes of this disclosure, optics do not generally include planar or substantially planar transmissive elements such as transmissive windows or films, such as those that serve as transmissive aperture that protect internal components.

Some example indirect exposure embodiments are discussed below with reference to FIGS. 9-14.

Other embodiments of device 10 do not include any optics 16 downstream of laser diode 14 for affecting or treating the beam. Such embodiments are referred to herein as "direct exposure" embodiments. A "direct exposure" embodiment or configuration does not include any optics downstream of laser diode for affecting or treating the beam(s) generated by laser diode. Some direct exposure devices may include a window (e.g., to protect the laser diode and/or other internal components of the device) that does not substantially affect the beam(s). A window may be formed from any suitable material, e.g., sapphire, quartz, diamond, or other material transparent at the frequency of the laser diode and preferably also having a good thermal coefficient. Some example direct exposure embodiments are discussed below with reference to FIGS. 15-18.

Because laser diodes typically emit a divergent beam, the laser diode 14 may be positioned very close to the application end 42 of the device that contacts the skin during treatment (and thus very close to the target surface). For example, some direct exposure embodiments are also configured for "close proximity" radiation, in which the "proximity gap spacing" is less than or equal to 10 mm. As used herein, the "proximity gap spacing" is defined as the distance between the emitting surface 80 of the laser diode 14 and the skin-contacting surface of device 10, i.e., the distance between the emitting surface 80 of the laser diode 14 and the skin when device 10 is in contact with the skin in a treatment position. In some embodiments, the proximity gap spacing is less than or equal to 5 mm, 2 mm, or even 1 mm. In particular embodiments, the proximity gap spacing is less than 500 µm, less than 200 µm, or even less than 100 µm. The proximity gap spacing may be selected based on one or more parameters, e.g., the desired size and/or intensity of treatment zones on the skin, and/or manufacturing constraints or costs.

It should be understood that "close proximity" embodiments of device 10 may include direct exposure embodiments (i.e., no optics downstream of the laser diode) in which the emitting surface 80 of laser diode 14 is located within 1 cm from the skin surface, as well as indirect exposure embodiments in which an optical element 16 (e.g., a fast axis cylindrical lens or a ball lens) is positioned very close to the laser diode 14 and to the application end 42 of the device 10 such that the emitting surface 80 of laser diode 14 and the optical element 16 are both located within 1 cm from the skin surface Control system 18 may be configured to control one or more components of device 10 (e.g., laser engine 12 and/or a beam scanning system 142). Control system 18 may include, for example, any one or more of the following: a laser control system for controlling aspects of the generation and delivery of laser beams to the user; in embodiments with a scanning system for scanning a beam to generate a pattern of treatment spots on the target skin area, a scanning system control system for controlling the scanning system; a displacement-based control system for controlling aspects of device 10 based on the determined displacement of device 10 across to the skin (e.g., as device is glided across the skin during treatment), e.g., relative to a prior treatment position; a temperature control system; an eye safety control system to help prevent exposure of the eyes (e.g., the corneas) to the treatment radiation (an eye safety control system may be omitted in embodiments in which the laser radiation emitted from device 10 is inherently eye-safe, e.g., certain direct exposure embodiments of device 10); and/or a battery/power control system.

Control system 18 may include one or more sensors 26, user interfaces 28 for facilitating user interaction with device 10, and control electronics 30 for processing data (e.g., from sensors 26 and/or user interfaces 28) and generating control signals for controlling various components of device 10. Control electronics 30 may include one or more processors and memory devices for storing logic instructions or algorithms or other data. Memory devices may include any one or more device for storing electronic data (including logic instructions or algorithms), such as any type of RAM, ROM, Flash memory, or any other suitable volatile and/or non-volatile memory devices. Logic instructions or algorithms may be implemented as software, firmware, or any combination thereof. Processors may include any one or more devices, e.g., one or more microprocessors and/or microcontrollers, for executing logic instructions or algorithms to perform at least the various functions of device 10 discussed herein. Control electronics 30 may include exclusively analog electronics or any combination of analog and digital electronics.

In some embodiments, control system 18 may include any of the various sensors and/or control systems disclosed in U.S. Ser. No. 13/366,246. For example, control system 18 may include one or more displacement sensor 100 (e.g., displacement sensor 100A, 100B, 100C, or 100D), motion/speed sensor 102, skin-contact sensor 104, pressure (or force) sensor 106, temperature sensor 108, radiation sensor 110, color/pigment sensor 112, eye safety sensor 114, dwell sensor 116, and/or roller-based sensor 118, as disclosed in U.S. Ser. No. 13/366,246. As another example, control system 18 may include any or all of a radiation source control system 130, a displacement-based control system 132, a user interface control system 134, a temperature control system 136, and/or a battery/power control system 138, as disclosed in U.S. Ser. No. 13/366,246.

Control system 18 may control components or aspects of device 10 based on feedback from sensors 26, user input received via user interfaces 28, and/or logic instructions/algorithms. For example, in some embodiments, control system 18 may control the operation of laser engine 12 and/or component(s) of a beam scanning system (e.g., a rotating scanning element) based at least on feedback from a displacement sensor for detecting the displacement of device 10 relative to the skin 40 as the device is moved across the skin. Thus, for example, control system 18 may control laser engine 12 and/ova rotating scanning element based on signals from a displacement sensor indicating that device 10 has moved a certain distance across target area 40 from a prior treatment position. As another example, control system 18 may control the operation of laser engine 12 and/or component(s) of a beam scanning system (e.g., a rotating scanning element) based at least on feedback from a glide speed sensor for detecting the speed of device 10 moving across the skin. Thus, for example, control system 18 may control laser engine 12 and/or a rotating scanning element based on signals from a glide speed sensor indicating that device 10 is moving at a particular speed across the skin 40.

More specifically, control system 18 may be configured to control one or more operational parameters of device 10. For example, control system 18 may control the treatment level (e.g., low power level, medium power level, or high power level) or treatment mode (e.g., gliding mode vs. stamping mode; or rapid-pulse mode vs. slow-pulse mode; or initial treatment mode vs. subsequent treatment mode; etc.), the status of laser diode 14 (e.g., on/off, pulse-on time, pulse-off time, pulse duty cycle, pulse frequency, temporal pulse pattern, etc.), parameters of the radiation (e.g., radiation wavelength, intensity, power, fluence, etc.), the configuration or operation of one or more optical elements (e.g., the operation of a rotating-element beam scanning system 142, as discussed below), and/or any other aspects of device 10.

Sensors 26 may include any one or more sensors or sensor systems for sensing or detecting data regarding device 10, the user, the operating environment, or any other relevant parameters. For example, as discussed in greater detail below with respect to FIG. 2, sensors 26 may include one or more of the following types of sensors: (a) one or more displacement sensor for determining the displacement of device 10 relative to the skin as device 10 is moved (e.g., glided) across the skin, (b) one or more glide speed sensor for determining the speed, rate, or velocity of device 10 moving (e.g., gliding) across the skin, (c) one or more skin-contact sensor for detecting proper contact between device 10 and the skin, (d) one or more pressure sensor for detecting the pressure of device 10 pressed against the skin, (e) one or more temperature sensor for detecting the temperature of the skin, a region of the skin, and/or components of device 10, (f) one or more radiation sensor for detecting one or more parameters of radiation (e.g., intensity, fluence, wavelength, etc.) delivered to the skin, (g) one or more color/pigment sensor for detecting the color or level of pigmentation in the skin, (h) one or more treatment endpoint sensor, e.g., a color/pigment sensor, for detecting an influence of the radiation on the skin (e.g., erythema, temperature, perifollicular edema, etc.) during or after a treatment, (i) one or more eye safety sensor for preventing unwanted eye exposure to light from laser diode 14, (j) one or more dwell sensor for detecting if the device is stationary or essentially stationary with respect to the skin, (k) one or more roller-type sensors for detecting the displacement and/or glide speed of device 10, and/or any (l) other suitable types of sensors.

User interfaces 28 may include any systems for facilitating user interaction with device 10. For example, user interfaces 28 may include buttons, switches, knobs, sliders, touch screens, keypads, devices for providing vibrations or other tactile feedback, speakers for providing audible instructions, beeps, or other audible tones; or any other methods for receiving commands, settings, or other input from a user and providing information or output to the user. User interfaces 28 may also include one or more displays 32, one or more of which may be touchscreens for receiving user input. One or more user interfaces 28 or portions thereof may be included in a separate housing from the treatment device, such as in a smart charging dock or a personal computer, and the treatment device may communicate with the separate housing via hardwire (such as a cable or jack), wireless methods (such as infrared signals, radio signals, or Bluetooth), or other suitable communication methods.

Power supplies 20 may include any one or more types and instances of power supplies or power sources for generating or supplying power to the various components of device 10. For example, power supplies 20 may comprise one or more rechargeable or non-rechargeable batteries, capacitors, super-capacitors, DC/DC adapters, AC/DC adapters, and/or connections for receiving power from an outlet (e.g., 110V wall outlet).

In some embodiments, power supplies 20 include one or more rechargeable or non-rechargeable batteries, e.g., one or more Li ion cells. In such embodiments, the cell voltage may range from about 2.8 to 3.8 V, depending on the specific cell chemistry and the battery charge state.

In some embodiments, the design or specifics of the multi-emitter laser diode 14 in device 10—for example, the number of emitter junctions formed in the laser diode 14—may be selected based on one or both of (a) the voltage of the relevant power supply (e.g., Li ion battery) and (b) the operational wavelength (e.g., 1400 nm to 1550 nm) of the laser. For example, the number of emitter junctions formed in laser diode 14 may be selected such that the intrinsic voltage drop of the laser diode 14 at the operational wavelength is close to, but not exceeding, a nominal voltage of the power supply. For instance, assume the following intrinsic voltage drops for laser diodes operating at a wavelength of 1400 nm to 1550 nm:

(a) 1.5V for a single-emitter laser diode,
(b) 2.5V for a dual-emitter laser diode 14, and
(c) 3.5V for a triple-emitter laser diode 14.

If the power supply is a rechargeable Li ion battery having a nominal voltage of 3.3V, the dual-emitter laser diode 14 may be selected because it more closely matches the battery voltage as compared to the single-emitter laser diode, and because the voltage of the triple-emitter laser diode 14 exceeds the battery.

Figure 2:
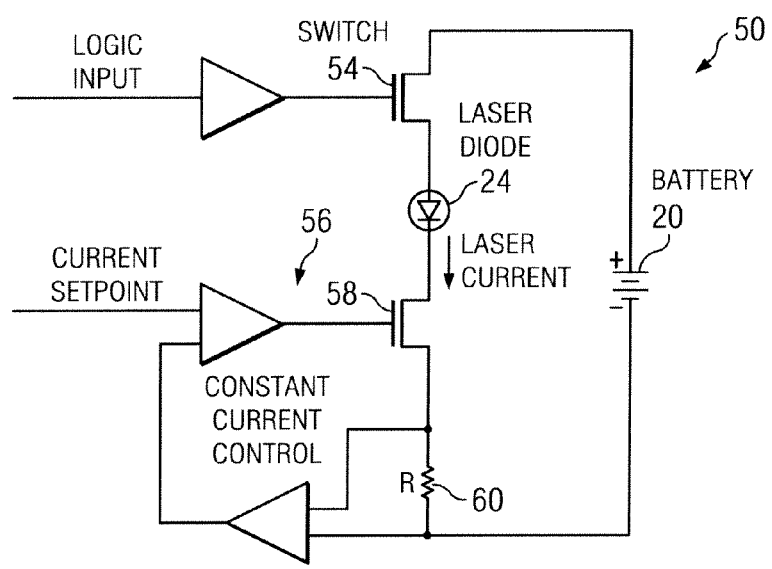
FIG. 2 illustrates an example constant-current laser diode driver circuit of the device shown in FIG. 1, according to certain embodiments of the present disclosure.

FIG. 2 illustrates an example constant-current laser diode driver circuit 50 (or "laser control circuit") of device 10 shown in FIG. 1, according to certain embodiments of the present disclosure. As shown, laser control circuit 50 includes a rechargeable battery 20, a transistor switch 54, a multi-emitter laser diode 14, and a constant-current controller 56 including a constant-current setting transistor 58 and a current-sense resistor 60, all connected in series. As discussed above, the multiple emitters of the multi-emitter laser diode 14 are also connected in series in the circuit.

Figure 3:
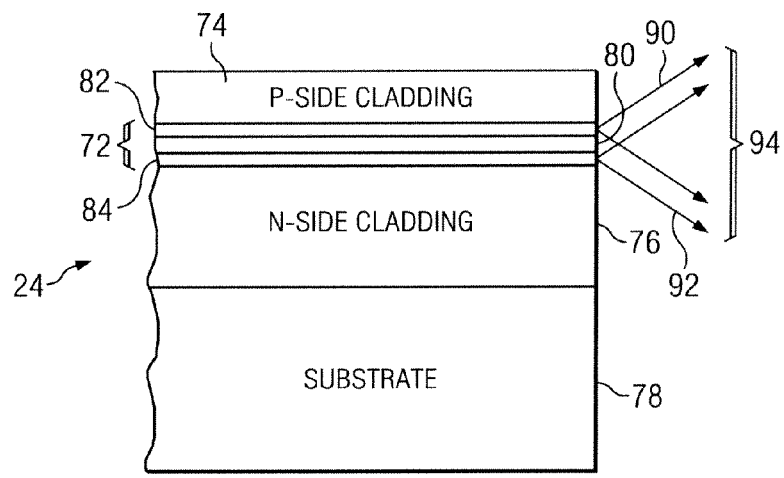
FIG. 3 illustrates a cross-sectional side view of an example multi-emitter laser diode, according to certain embodiments of the present disclosure.

FIG. 3 illustrates a cross-sectional side view of an example multi-emitter laser diode 14, according to certain embodiments of the present disclosure. In particular, FIG. 3 illustrates an example dual-emitter laser diode 14. Dual-emitter laser diode 14 includes a monolithic laser diode stack structure 70 including a multiple-emitter region 72 formed between a p-doped cladding region 74 and an n-doped cladding region 76, all formed on a single substrate 78.

In the illustrated example, multiple-emitter region 72 defines two emitter junctions, 82 and 84, each configured to emit a laser beam from an emitting surface 80. In other examples, multiple-emitter region 72 defines more than two (e.g., three, four, or more) emitter junctions. In some embodiments, multiple-emitter region 72 may comprise a stacked multiple quantum well (MQW) active emitters region.

Emitter junctions 82 and 84 may be spaced apart from each other (in a stacked manner) by any suitable distance. For example, emitter junctions 82 and 84 may be spaced apart from each by about 2 µm to about 10 µm. In some embodiments, emitter junctions 82 and 84 are spaced apart by about 5 µm.

Multiple-emitter region 72, p-doped cladding region 74, n-doped cladding region 76, and substrate 78 may be formed from any suitable materials. At least some of such materials may be selected based on the operational wavelength of the laser diode. For example, for a wavelength in the 1400 nm to 1550 nm range, multiple-emitter region 72 may be formed from different indium gallium arsenide phosphide (InGsAsP) composition, and cladding regions 74 and 76 and substrate 78 may be formed from indium phosphide (InP) compositions. As another example, the multiple quantum wells region 72 can also be formed from different aluminum gallium indium arsenide (AlGaInAs) in the similar wavelength range.

When dual-emitter laser diode 14 receives suitable power from power supply 20, each emitter junction 82 and 84 emits an individual laser beam, indicated as beams 90 and 92, respectively. The individual beams 90 and 92 at least partially combine or interact to form a collective beam 94.

Each beam 90 and 92 diverges faster in a first axis, referred to as the fast axis (indicated in FIG. 3), than in an orthogonal second axis, referred to as the slow axis (extending into the page of FIG. 3). As a result, the collective beam 94 also diverges faster in the first axis than in the slow axis.

Figure 4:
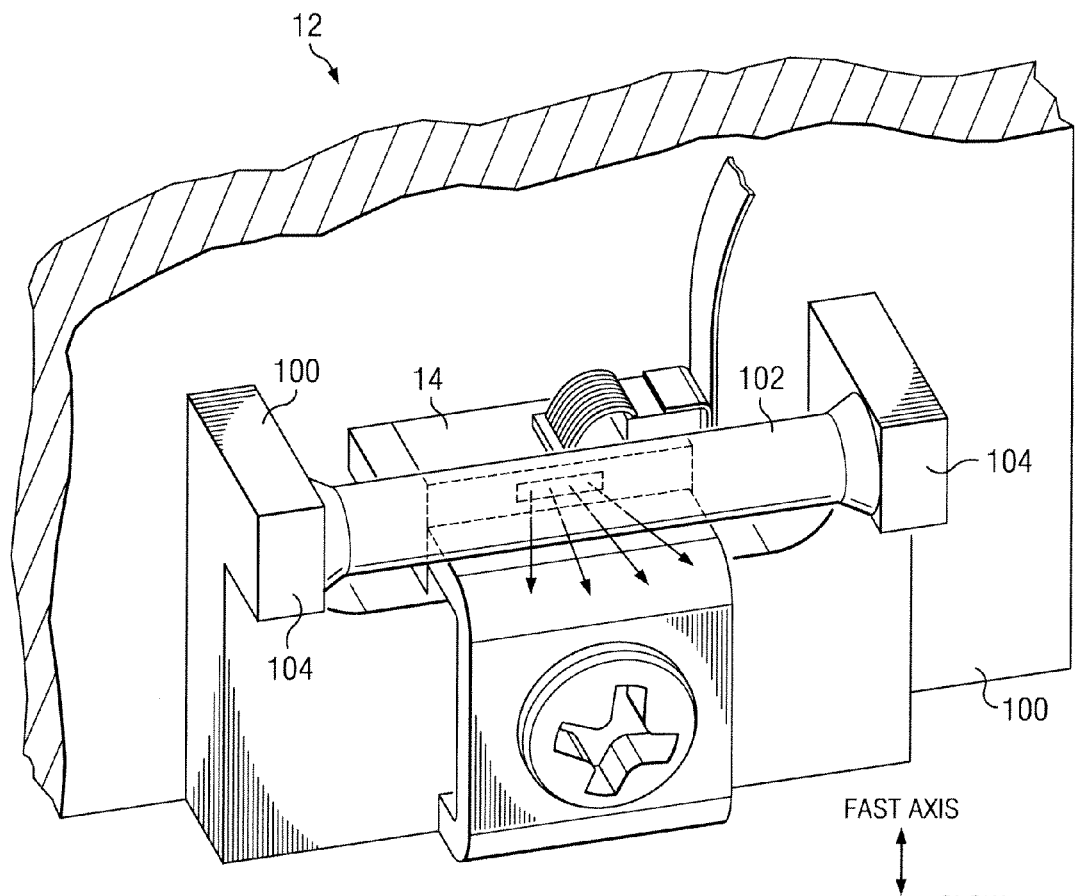
FIG. 4 illustrates a three-dimensional view of a portion of an example laser engine, according to certain embodiments of the present disclosure.

FIG. 4 illustrates a three-dimensional view of a portion of an example laser engine 12, according to certain embodiments of the present disclosure. Laser engine 12 may include multi-emitter laser diode 14, a heat sink 100, a fast axis optic 102, and a securing system 104 for securing fast axis optic 102. Laser engine 12, in particular heat sink 100, may be mounted or connected to a printed circuit board (PCB). laser diode 14 may be coupled to electronics on PCB by a suitable electrical connection, e.g., a flexible cable.

In this example, laser diode 14 is a dual-emitter laser diode 14 (e.g., with a structure as shown in FIG. 3), each emitter having a junction or aperture extending lengthwise in the slow axis direction. For example, each emitter may be approximately 100 µm by 1 µm.

Heat sink 100 serves to cool laser diode 14 and may be fabricated via an extrusion process or in any other suitable manner. Some embodiments include one or more fans to help maintain the laser temperature at a desired level. Heat sink may include fins or other structures for promoting heat transfer. In some embodiments the heat sink may be passive and/or absorb and/or transfer heat by conduction only and/or combined with natural convection and/or combined with radiative heat transfer. In some embodiments, heat sink 100 in the fully assembled device 10 has a rating of about 2.5° C./W or lower. In particular embodiments, heat sink 100 in the fully assembled device 10 has a rating of about 1.5° C./W or lower.

In some embodiments, device 10 may also include one or more fans 34 to actively cool heat sink 100, to further promote heat transfer from laser diode 14 and/or other powered components of device 10.

Fax axis optic 102 may comprise any optic for affecting the fast-axis profile of collective beam 94 emitted from multi-emitter laser diode 14. For example, in the illustrated embodiment, fast axis optic 102 is a high numerical aperture (high NA) short focal length cylindrical lens (or "rod lens") arranged to reduce the angular divergence of collective beam 94 in the fast axis. In one embodiment, cylindrical lens 102 is about 12 mm long with a diameter of about 2 mm. However, lens 102 may have any other suitable dimensions. Further, in other embodiments, lens 102 may comprise a different shaped lens. For example, lens 102 may be an aspheric lens or a spherical lens.

Lens 102 may be secured to heat sink 100 in any suitable manner. For example, lens 102 may be mounted between a pair of support structures, which form a securing system 104 for securing the cylindrical lens 102 to heat sink 100. The support structures of securing system 104 may be integral with the body of heat sink 100, or otherwise coupled to heat sink 100. Lens 102 may be secured to the support structures in any suitable manner. For example, lens 102 may be positioned between the support structures and adhered to the support structures using UV adhesive, e.g., UV epoxy that is cured via a UV curing process. Cylindrical lens 102 may be positioned at any suitable distance from the emitter junctures/apertures of laser diode 14. In one embodiment, lens 102 is positioned about 260 um from the emitter junctures/apertures of laser diode 14.

Figure 5:
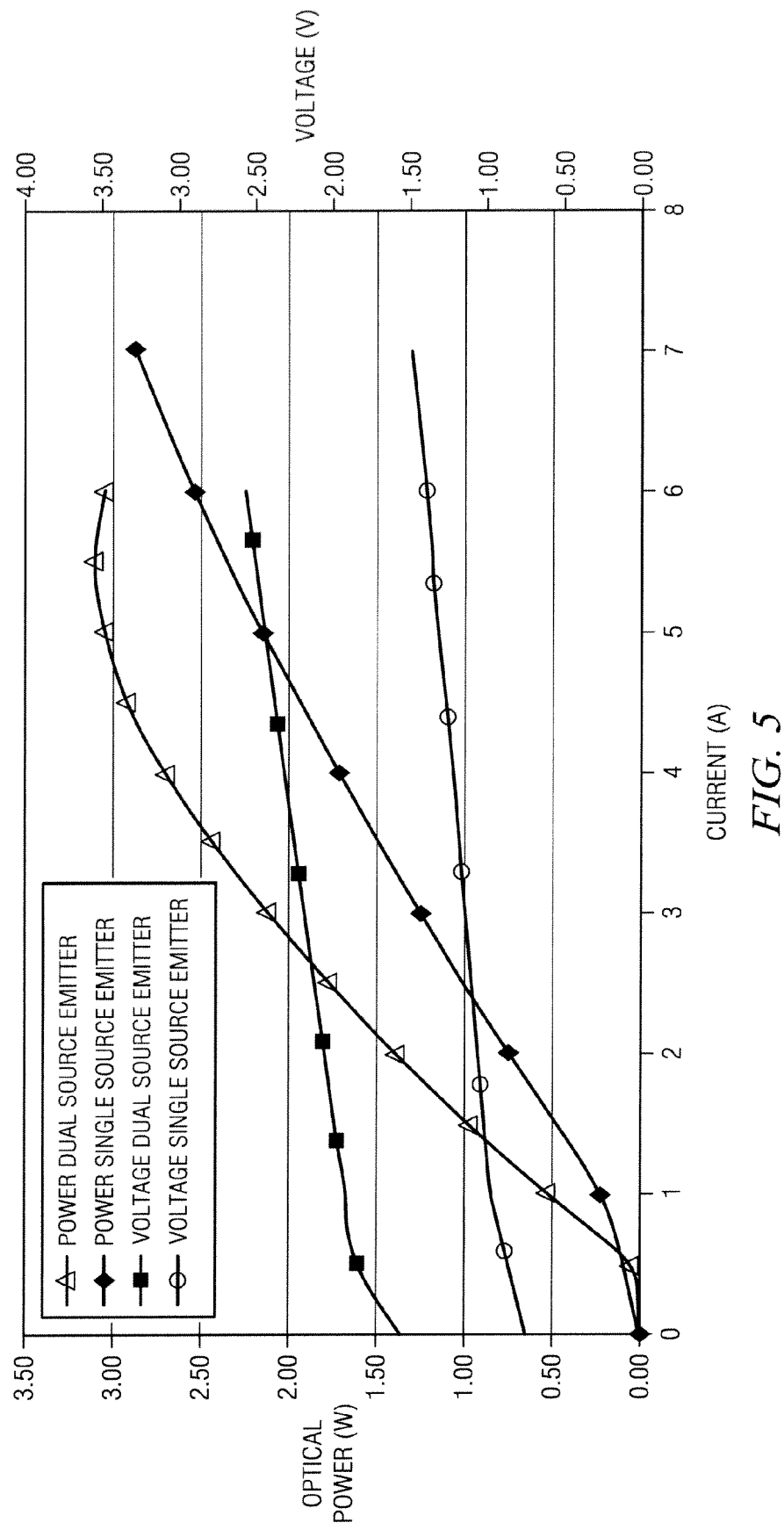
FIG. 5 is a graph indicating PIV (Power-Current-Voltage) characteristics for (a) an example dual-emitter laser diode according to embodiments of the present disclosure and (b) a typical single-emitter laser diode.

FIG. 5 is a graph indicating PIV (Power-Current-Voltage) characteristics for (a) an example dual-emitter laser diode 14 according to embodiments of the present disclosure and (b) a typical single-emitter laser diode, both operating at the example wavelength range of 1440 nm at approximately 23° C. In particular, the graph indicates the optical output power (W) and forward voltage drop (V) corresponding to a range of fixed drive current values (A) for a laser diode arranged in a circuit similar to circuit 50 shown in FIG. 2.

As shown, both the optical output power and higher forward voltage drop are significantly higher for the example dual-emitter laser diode 14 than for the single-l0 emitter laser diode. As discussed above, wherein device 10 is battery-powered, it may be desirable to closely match the forward voltage drop of the laser diode with the voltage of the battery (without exceeding the battery voltage). Thus, for battery voltages above the dual-emitter laser diode 14 forward voltage drop line shown in FIG. 5, the dual-emitter laser diode 14 may provide significantly increased efficiency performance as compared with the single-emitter laser diode.

Thus, multi-emitter laser diodes 14 may be configured or selected to provide increased or desired efficiency performance for device 10. For example, a multi-emitter laser diode 14 is powered by a rechargeable battery 20 having a nominal voltage, and laser control circuit 50 powers the laser diode 14 such that a forward voltage drop of the laser diode 14 during normal operation is at least 50% of the nominal voltage of the rechargeable battery 20. For instance, in embodiments in which the nominal voltage of the rechargeable battery 20 is between about 2.8V and about 3.8V, and laser control circuit 50 may power multi-emitter laser diode 14 such that the forward voltage drop of the laser diode 14 is at least 1.8V. In some embodiments, the forward voltage drop of the laser diode 14 during normal operation is at least 65% of the nominal voltage of the rechargeable battery 20. In particular embodiments, the forward voltage drop of the laser diode 14 during normal operation is at least 80% of the nominal voltage of the rechargeable battery 20.

With reference to FIG. 5, in some embodiments, laser control circuit 50 provides a fixed drive current of between about 1 A and about 6 A to a multi-emitter laser diode 14, the output power of the laser diode 14 is between about 0.5 W and about 3.1 W, and the voltage drop of the laser diode 14 is between about 1.9V and about 2.6V. In particular embodiments, laser control circuit 50 provides a fixed drive current of between about 3 A and about 5 A to a multi-emitter laser diode 14, the output power of the laser diode 14 is between about 2.15 W and about 3.0 W, and the voltage drop of the laser diode 14 is between about 1.9V and about 2.6V. In one embodiment, laser control circuit 50 provides a fixed drive current of about 4.5 A.

For embodiments of device 10 that utilize a Li ion battery cell having a nominal cell voltage between about 2.8V and 3.8V (depending on the specific cell chemistry and the battery charge state), the voltage drop of the dual-emitter laser diode 14 matches the cell voltage significantly better than does the single-emitter laser diode. Thus, as shown in FIG. 5, a significantly lower drive current may be used to achieve the same optical output power by using the dual-emitter laser diode 14 instead of the single-emitter laser diode.

In an example embodiment, the optical output power required for the desired treatment is about 2.5 Watts. As shown in FIG. 5, to provide an optical output power of 2.5 Watts, the single-emitter laser diode requires a current of about 5.8 amps and has a corresponding forward voltage drop of about 1.4 V, whereas the dual-emitter laser diode 14 requires a current of about 3.6 amps and has a corresponding forward voltage drop of about 2.25 V. Thus, in this example, the current is reduced by about 38% by using the dual-emitter laser diode 14 instead of the single-emitter laser diode.

Further suppose the laser is powered by a Li ion cell having a nominal voltage of 3.7V. Thus, the difference in voltage between the battery and the respective laser diode is 2.3 V for the single-emitter laser diode, or 1.45 V for the dual-emitter laser diode 14. Thus, in this example, the excess voltage lost to waste heat is reduced by about 37% by using the dual-emitter laser diode 14 instead of the single-emitter laser diode.

Figure 6A:
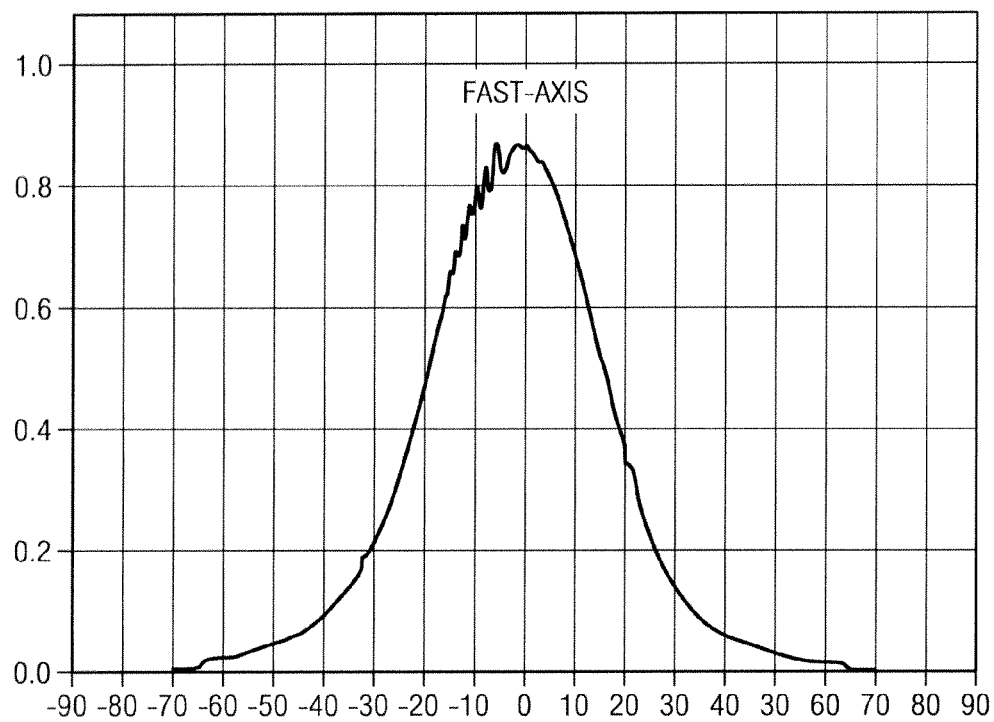
FIGS. 6A and 6B illustrate measured far-field beam angular profiles of an example dual-emitter laser diode in the fast-axis direction (FIG. 6A) and the slow-axis direction (FIG. 6B).
Figure 6B:
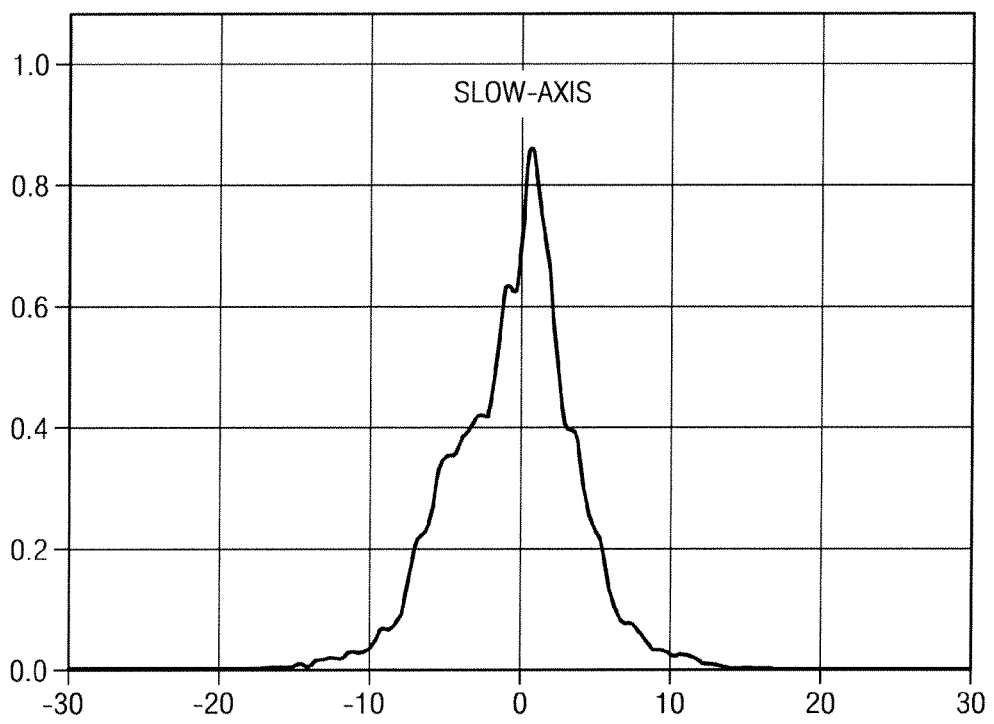

FIGS. 6A and 6B illustrate measured far-field beam angular profiles of an example dual-emitter laser diode 14 in the fast-axis direction (FIG. 6A) and the slow-axis direction (FIG. 6B). The illustrated angular profiles are similar to the corresponding fast-axis and slow-axis angular profiles for a single-emitter laser diode according to similar operating parameters.

Thus, for embodiments of device 10 in which dual-emitter laser diode 14 is positioned very close to the target surface during treatment, e.g., "close proximity" embodiments in which the emitting surface of the dual-emitter laser diode 14 is positioned less than 1 cm from the target surface, the beam profile delivered to the target surface may be substantially similar to the beam profile delivered by a single-emitter diode. Additionally, due to the very close proximity of the stacked dual emitters to each other (e.g., a few micrometers), the direct exposure beam spot size at the treatment plane may be virtually identical to that of a single-emitter laser diode.

Figure 7A:
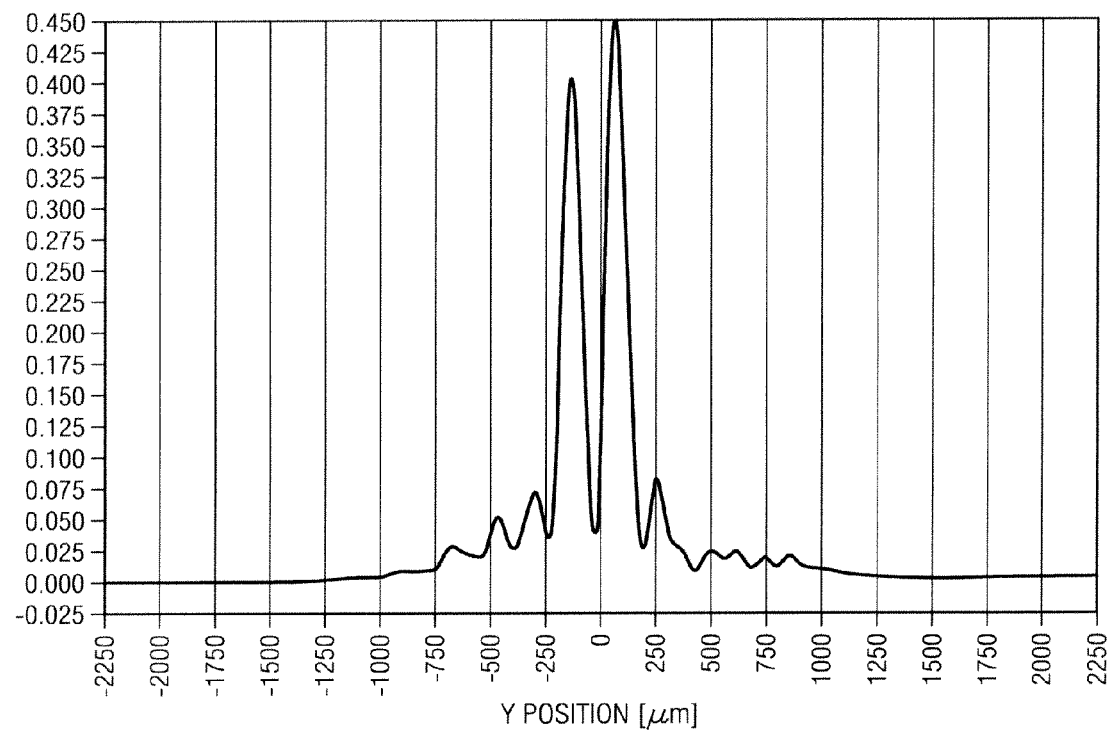
FIGS. 7A and 7B illustrate measured target plane beam profiles of an example dual-emitter laser diode in the fast-axis direction (FIG. 7A) and the slow-axis direction (FIG. 7B).
Figure 7B:
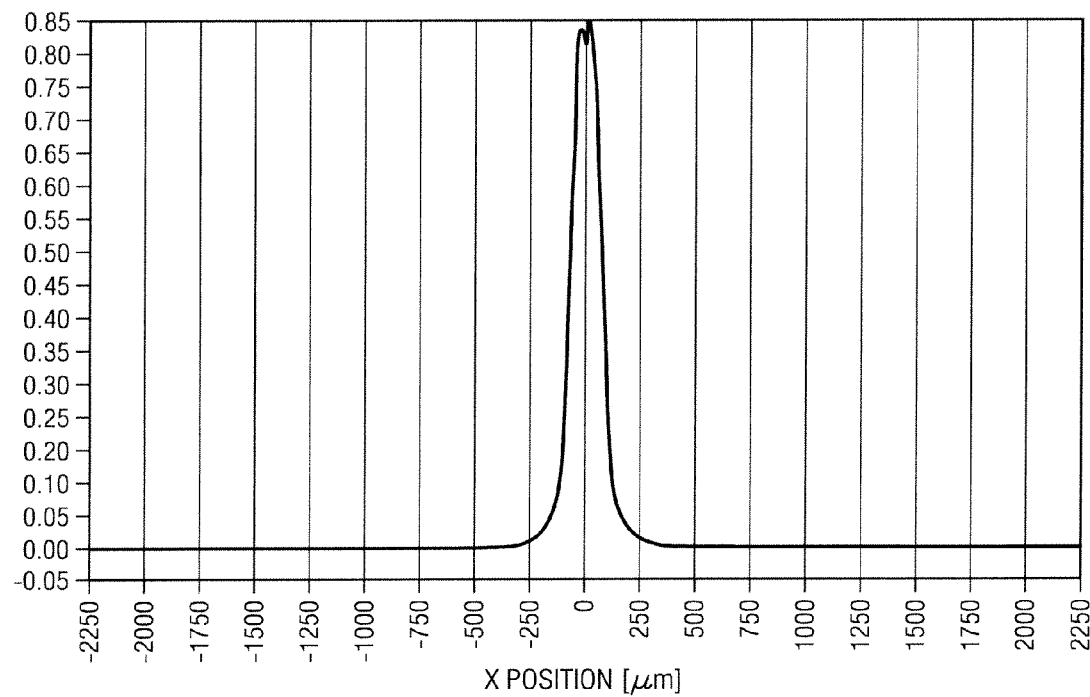

FIGS. 7A and 7B illustrate measured target plane beam profiles of an example dual-emitter laser diode 14 in the fast-axis direction (FIG. 7A) and the slow-axis direction (FIG. 7B). The fast-axis profile shows closely spaced double beams, which is the magnified near-field image of the dual emitters of dual-emitter laser diode 14. In other words, each peak in the fast-axis profile corresponds with the individual beam 90 or 92 emitted by one of the two emitter junctions of dual-emitter laser diode 14.

Thus, certain embodiments of device 10 in which dual-emitter laser diode 14 is not positioned very close to the target surface during treatment, referred to herein as "remote proximity" embodiments, may include fast axis optics 16 for refocusing or otherwise treating the fast axis profile of the beam before reaching the target surface, e.g., as discussed with respect to FIGS. 8A-8D below. In this context, "remote proximity" refers to a proximity gap spacing (i.e., the distance between the emitting surface 80 of laser diode 14 and the target skin surface) of more than 1 cm.

Figure 8A:
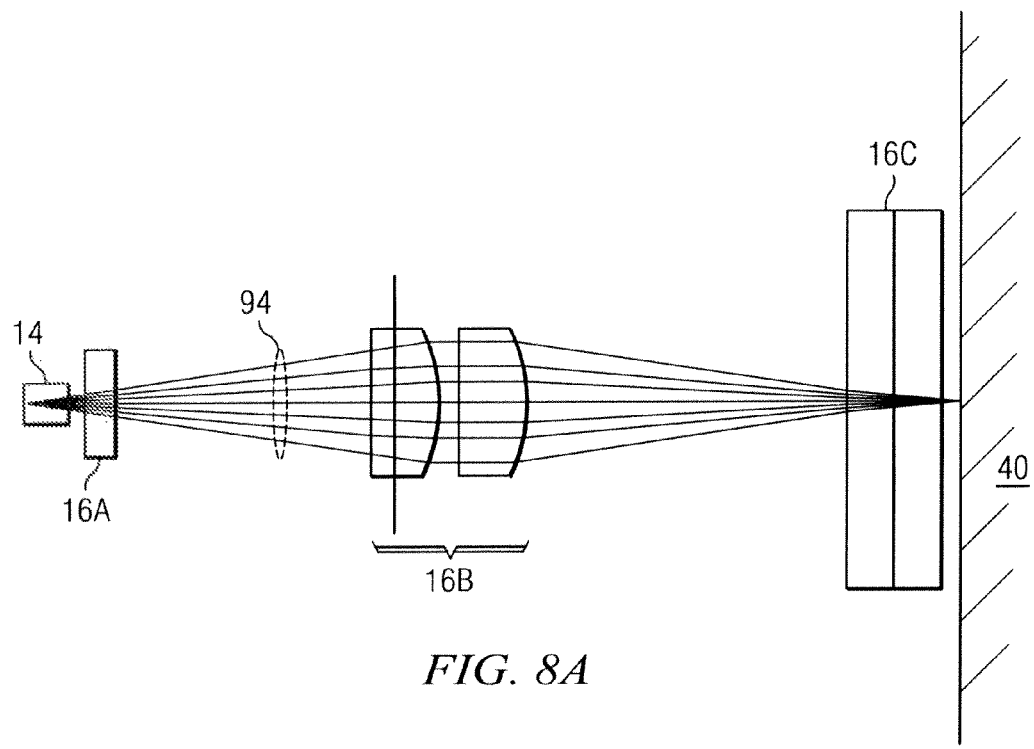
FIGS. 8A-8F illustrate an example arrangement including a dual-emitter laser diode and downstream optics, and resulting (simulated in 8B-8D; measured actual in 8E and 8F) beam profiles at the target surface, for an example remote proximity embodiment of the laser-based treatment device.

FIGS. 8A-8D illustrate an example arrangement including a dual-emitter laser diode 14 and downstream optics 16, and the resulting (simulated) beam profiles at the target surface, for an example remote proximity embodiment of device 10. In particular, FIG. 8A shows an example arrangement including a dual-emitter laser diode 14, first fast-axis optic 16A located immediately downstream of dual-emitter laser diode 14, slow-axis optic 16B, and second fast-axis optic 16C located proximate the application end 42 of device 10.

Fast-axis optic 16A may comprise any optical element(s) for treating the rapidly divergent fast axis profile of beam 94 emitted from laser diode 14 (and may or may not additionally treat the fast axis profile of beam 94). For example, fast-axis optic 16A may comprise a cylindrical lens such as cylindrical lens 102 discussed above, or alternatively, a spherical or aspheric lens.

Slow-axis optic 16B may comprise any optical element(s) for treating the divergent slow axis profile of beam 94 emitted from laser diode 14 (and may or may not additionally treat the fast axis profile of beam 94). For example, slow-axis optic 16B may comprise one or more cylindrical, spherical, or aspheric lens. In some embodiments, slow-axis optic 16B comprises lenses or other optics of a beam-scanning system. For example, as discussed below with reference to FIGS. 11A-14, a beam-scanning system may include a rotating element having multiple optical deflection sectors, or facets, that successively pass through beam 94 to provide a time-sequential series of output beams directed toward the application end 42 of device 10, the series of output beams being offset (angularly and/or translationally) from each other such that the series of output beams form an array of treatment spots on the target surface.

Fast-axis optic 16C may comprise any optical element(s) for treating the fast axis profile of beam 94 before delivery to the target surface. In particular, fast-axis optic 16C may comprise any optical element(s) configured to refocus the dual fast-axis beamlets (or intensity peaks) shown in FIG. 7A into a single beam (or intensity peak). For example, fast-axis optic 16C may comprise a cylindrical lens, a spherical lens, or an aspheric lens.

Figure 8B:
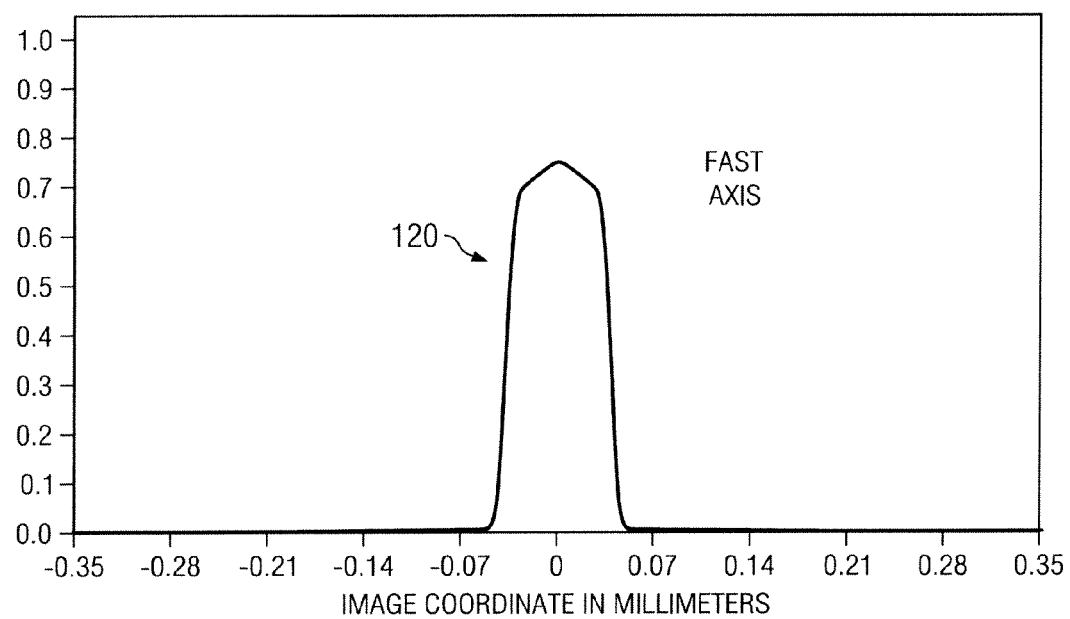

FIG. 8B illustrates an example graph 120 of the fast-axis beam profile at the target surface, for the device arrangement of FIG. 7A. As shown, fast-axis optic 16C refocuses the dual fast-axis beamlets or intensity peaks shown in FIG. 7A into a single beam or intensity peak, which may be advantageous for providing a treatment spot having desired characteristics.

Figure 8C:
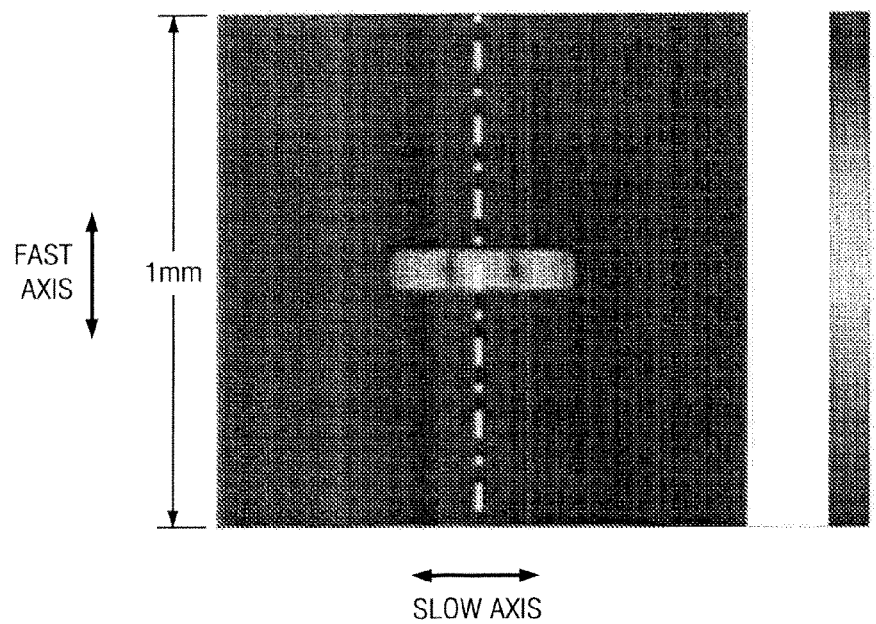

FIG. 8C illustrates an example two-dimensional intensity profile of beam 94, measured at the target plane, showing the intensity profile in both the fast-axis and slow-axis.

Figure 8D:
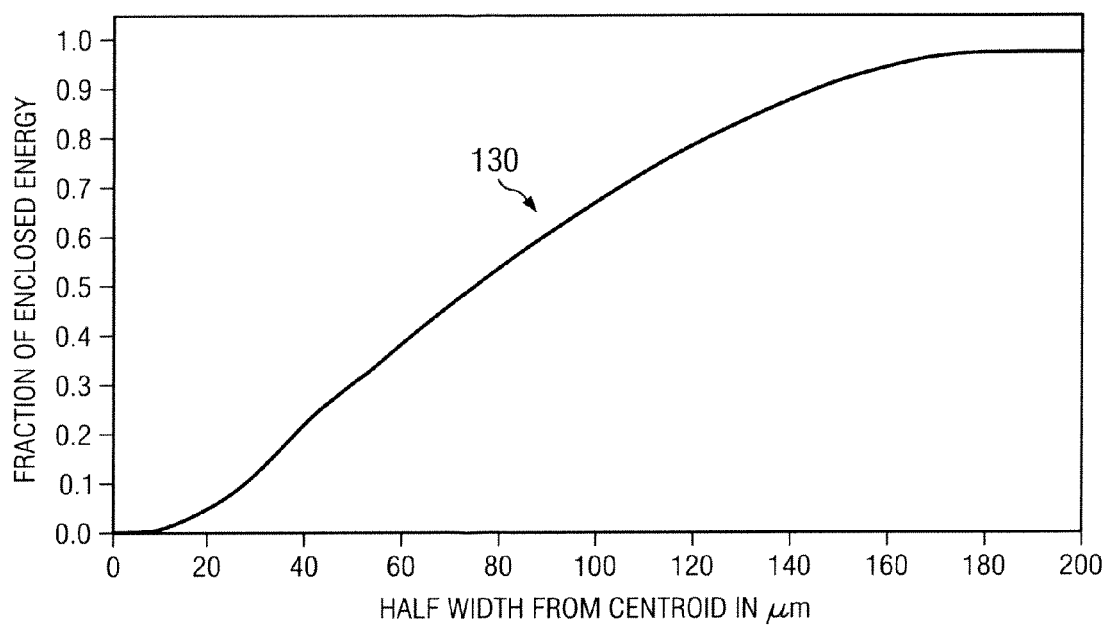

FIG. 8D illustrates a graph 130 of the fraction of the energy delivered to the target surface that is delivered within a square of a defined size on that target surface. The energy delivered within the square is referred to as the "ensquared energy." The graph shows the fraction of ensquared energy as a function of square size for the example beam shown in FIG. 8C. The square size is defined in terms of half width from a centroid of the intensity profile plane, e.g., point C indicated in the intensity profile plane shown in FIG. 8C. Thus, a half width of 50 µm in graph 130 refers to a 100 µm×100 µm square centered around centroid C.

As shown in graph 130, the greater the half width (i.e., the larger the square), the greater the ensquared energy of the beam 94. For example, at a half width of 50 µm, the fraction of ensquared energy is about 0.30. At a half width of 100 µm, the fraction of ensquared energy is about 0.67. At a half width of 150 µm, the fraction of ensquared energy for the on-axis beam is about 0.92. At a half width of 200 µm, the fraction of ensquared energy for the on-axis beam is about 0.98. Thus, in embodiments or applications in which a treatment spot diameter or width of about 400 µm (i.e., 200 µm half width) is desired, a corresponding fractional ensquared energy of about 0.98 may be provided.

Figure 8E:
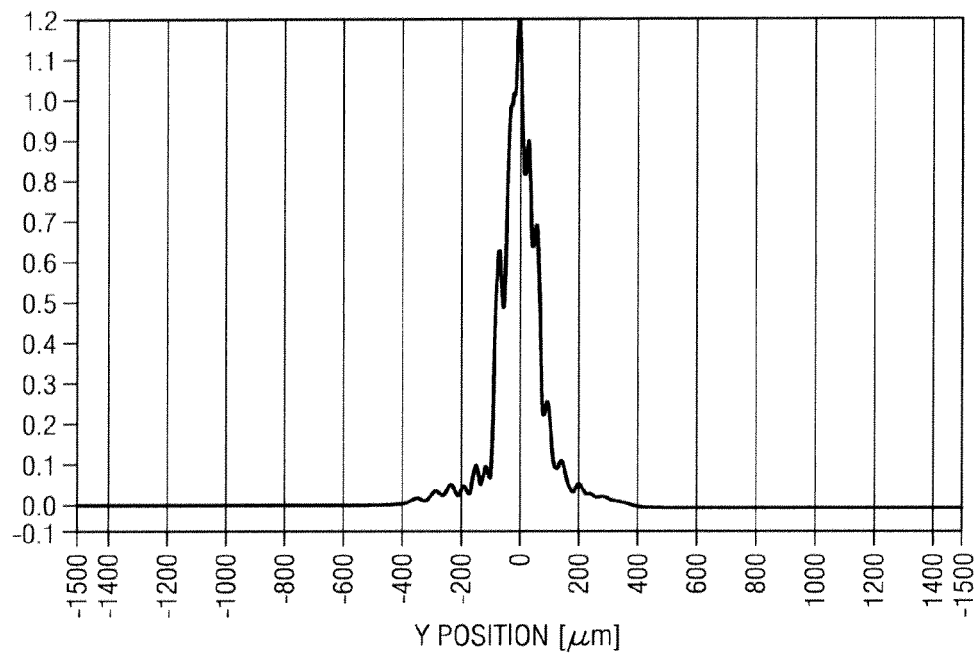
Figure 8F:
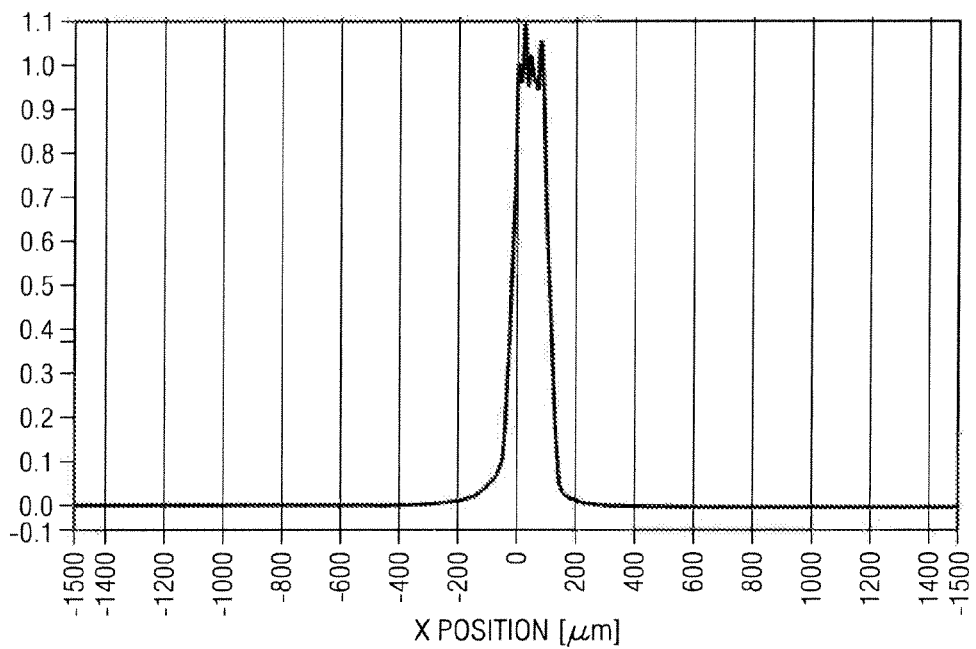

FIGS. 8E and 8F illustrates measured actual target beam profiles in the fast axis direction (FIG. 8E) and the slow axis direction (FIG. 8F) for an example embodiment of device 10 incorporating a fast-axis optic 16C embodied as a cylindrical lens near the target plane. The fast axis profile shown in FIG. 8E indicates the refocusing of the dual fast axis beamlets (shown in FIG. 7A) into a single beam by the cylindrical rod lens 16C near the target plane. In this example, the final collective beam is essentially a single 200-µm wide spot at the target surface in both the slow axis and fast axis directions.

Operation of Device 10

As discussed above, device 10 is configured to deliver one or more laser beams 94 to a target area 40 to provide a desired treatment. Device 10 may deliver beam(s) 94 to generated continuous lines or treatment spots on the target area 40. Treatment spots may be provided by pulsing the laser diode 14 and/or scanning the laser beam from laser diode 14 using a scanning device, as discussed below. In some embodiments, device 10 is configured to provide treatment spots that are spaced apart from each other by areas of non-irradiated skin between adjacent treatment spots, to provide a fractional treatment.

As used herein, a "treatment spot" (e.g., treatment spot 150 shown in FIG. 12) means a contiguous area of skin irradiated by multi-emitter laser diode 14—during a continuous period of irradiation or during a pulse—to a degree generally sufficient to provide a desired treatment in the skin at that location. Treatment spots may have any suitable size and/or shape depending on the particular embodiment, configuration, and/or application of the device. For example, treatment spots may have any suitable diameter, length, width, or other dimension. Some example shapes of treatment spots include: generally circular, generally elliptical, generally rectangular, linear line segments, curved arc segments, etc. The boundaries of a treatment spot may be defined by the "$1/e^2$ width," i.e., the treatment spot includes a contiguous area of the skin surface that is irradiated by a radiation intensity equal to at least $1/e^2$ (or 0.135) times the maximum radiation intensity at any point on the skin surface. Further, reference to a treatment spot "on the skin," "on target area 40," or similar language refers to radiation pattern on the skin which generally produces a radiation pattern within the skin, whether or not it produces a treatment effect on the surface of the skin.

Each treatment spot on the surface of the skin may produce a three-dimensional volume of thermally damaged skin extending below the surface of the skin, which may be referred to as a micro thermal spot (MTZ). Each MTZ may extend from the skin surface downward into the skin, or may begin at some depth below the skin surface and extend further downward into the skin, depending on the embodiment, device settings, or particular application. The lateral dimensions of each MTZ may be co-extensive with the dimensions of the corresponding irradiated treatment spot, may be smaller than the corresponding irradiated treatment spot, or may be larger than the corresponding irradiated treatment spot (e.g., due to thermal conductivity).

In some embodiments, device 10 is configured to be used in a "gliding mode" in which the device is manually dragged or glided across the skin while delivering pulsed and/or scanned radiation to the target area 40, to create rows or arrays of treatment spots on the skin. For example, in direct exposure embodiments, laser diode 14 may be pulsed while the device is manually dragged or glided across the skin by the user, to provide a row of treatment spots. The device may be glided multiple times across the skin to provide a two-dimensional array of treatment spots.

As another example, certain indirect exposure embodiments include an automated beam-scanning system that repeatedly scans a beam generated by laser diode 14 to provide a time-sequential series of output beams that are delivered to the skin, the series of output beams being offset (angularly and/or translationally) from each other such that a row or array of treatment spots are generated on the skin for each scan of the beam-scanning system (e.g., each revolution of a rotating multi-faceted scanning element). Device 10 may be glided across the target area 40 in a direction generally transverse to the direction of scanning provided by the beam-scanning system, such that the combination of the manual gliding and automated beam scanning results in a two-dimensional array of treatment spots generated on the skin for each glide of the device across the skin.

In other embodiments, device 10 is configured to be used in a "stamping mode" in which device 10 is held relatively stationary at different locations on the skin. At each location on the skin, device 10 may deliver one or more beams (or one or more automatically scanned rows or arrays of beam) to the skin to generate one or more treatment spots. Thus, device 10 may be positioned at a first location, one or more treatment spots may then be delivered to the skin while device 10 is held relatively stationary, device 10 may then be moved—by lifting device 10 and repositioning it or by gliding device 10 across the surface of the skin—to a new location, and one or more treatment spots may then be delivered at that location, and so on, in order to cover a target area 40 as desired.

For any of the various embodiments discussed above, device 10 (in particular, laser diode(s) 14) may be configured or operated to deliver radiation in any suitable manner. For example, in some embodiments, device 10 controls multi-emitter laser diode(s) 14 to provide CW or quasi-CW radiation, e.g., for bulk heating skin tightening, hair removal, or acne treatment by operating device 10 in a gliding mode.

In other embodiments, device 10 provides pulsed radiation. Pulsed radiation may include manually pulsed radiation or automatically pulsed radiation. In manually pulsed radiation, each pulse may be manually triggered, e.g. by pressing a button to initiate each pulse. In some embodiments, manually pulsed radiation used in a stamping mode. Manually pulsed radiation may be used for any suitable treatment, e.g., certain hair removal treatments.

Alternatively, in automatically pulsed radiation, pulses may be initiated or controlled automatically, e.g., according to a predefined pulse frequency or automatically upon some triggering event, such as automatic pulse triggering upon (e.g., a predetermined displacement of device 10 moving across the skin, or automatic pulse triggering upon re-triggering of a capacitive skin contact sensor by lifting and placing the device tip on a different spot, for example). Automatically pulsed radiation may be provided in any suitable manner, e.g., by controlling laser diode 14, by intermittently blocking the energy beam emitted by laser diode 14, or otherwise. Such embodiments may utilize any suitable pulse parameters, e.g., pulse rate or frequency, pulse on time, pulse off time, duty cycle, pulse profile, etc. In some embodiments, laser diode 14 may be pulsed at a rate between 0.5 and 75 Hz. For example, laser diode 14 may be pulsed at a rate between 2 and 30 Hz. In particular embodiments, laser diode 14 may be pulsed at a rate between 10 and 20 Hz, e.g., about 15 Hz. The energy per pulse on a given treatment zone can be achieved by a single pulse or by multiple repetitive pulses. Automatically pulsed radiation may be used for any suitable treatment, e.g., fractional treatment.

As used herein, a "pulse" may include both (a) a single, continuous burst of radiation from laser diode(s) 14, and (b) one or more higher-frequency pulses at substantially the same location on the skin (i.e., with substantially overlapping areas of irradiation at the skin surface), sometimes referred to as a modulated pulse, pulse train, or super pulse. If the time interval between the pulses in a pulse train is shorter than the relaxation time of the mechanism of action (e.g., shorter than the thermal relaxation time of a photothermolysis chromophore target), then the pulse train can deliver substantially similar results as a single longer pulse.

Embodiments with Beam Scanning System

Figure 9:
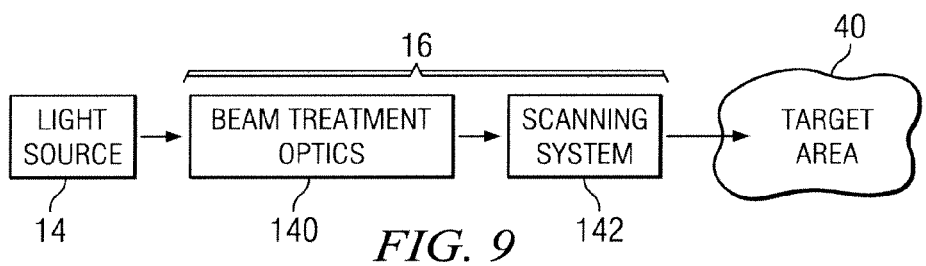
FIG. 9 illustrates aspects of an example laser-based treatment device including multi-emitter laser diode(s) and a beam-scanning system, according to certain embodiments.

FIG. 9 illustrates aspects of an example laser-based treatment device 10 including multi-emitter laser diode(s) 14 and a beam-scanning system, according to certain embodiments. In such embodiments, optics 16 may include beam treatment optics 140 and a scanning system 142. Beam treatment optics 140 may include any one or more optical elements, such as lenses, mirrors, and other reflective and/or fully or partially transmissive elements, for controlling one or more optical parameters of the radiation generated by laser diode(s) 14, such as the direction, shape (e.g., convergent, divergent, or collimated), and/or intensity profile of the radiation.

Scanning system 142 may be configured to scan an individual light beam (or multiple individual light beams) generated by laser engine 12 into a sequentially-delivered array of beams to create a pattern of treatment spots 150 (e.g., spots, lines, or other shapes) on the target area 40.

Figure 10:
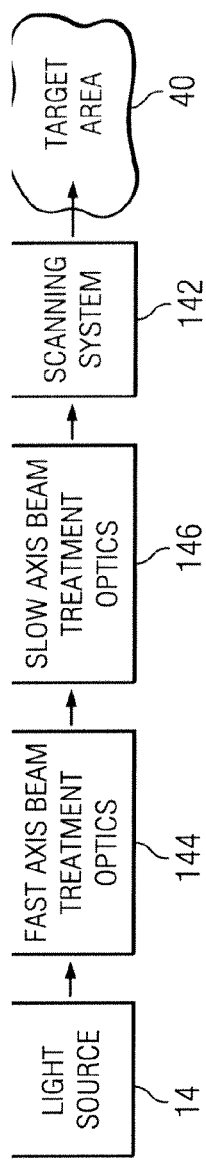
FIG. 10 illustrates example aspects of the beam treatment optics of a laser-based treatment device, according to certain embodiments.

FIG. 10 illustrates example aspects of the beam treatment optics 140 of a laser-based treatment device 10, according to certain embodiments. Beam treatment optics 140 may include axis-asymmetric elements that act on different optical axes of an incident light beam differently. For example, beam treatment optics 140 may include first optics configured to influence an incident light beam primarily in a first optical axis, and second optics configured to influence the light beam in a second optical axis orthogonal to the first axis. Influencing the beam along a particular optical axis may include affecting the intensity profile of the beam along the particular optical axis. As used herein, the intensity profile of the beam along a particular optical axis refers to the shape of the intensity profile along the particular optical axis (e.g., Gaussian, flat-topped, etc.); whether the beam is converging, diverging, or collimated; the degree of convergence or divergence of the beam; etc.

Thus, in the example embodiment shown in FIG. 10, beam treatment optics 140 include separate fast axis beam treatment optics 144 (or fast axis optics 144) and slow axis beam treatment optics 146 (or slow axis optics 146). Fast axis optics 144 include one or more optical elements configured to affect the intensity profile of the beam in the fast axis, while slow axis optics 146 include one or more optical elements configured to affect the intensity profile of the beam in the slow axis. In certain embodiments, fast axis optics 144 are configured to affect the fast axis intensity profile without substantially affecting the slow axis intensity profile. Further, in certain embodiments, slow axis optics 146 are configured to affect the slow axis intensity profile without substantially affecting the fast axis intensity profile. In particular embodiments, both of these features are provided: fast axis optics 144 affect the fast axis intensity profile without substantially affecting the slow axis intensity profile, and slow axis optics 146 affect the slow axis intensity profile without substantially affecting the fast axis intensity profile.

Alternatively, fast axis optics 144 and slow axis optics 146 may be partially or fully integrated. For example, a particular optical element (e.g., mirror or lens) may affect both the fast axis and slow axis intensity profiles. Such element may be referred to as a multi-axes optical element, and may or may not be symmetrical about all axes (e.g. spherical). Some embodiments may include one or more multi-axes optical elements, along with one or more separate fast axis optical elements; or one or more multi-axis optical elements, along with one or more separate slow axis optical elements; one or more multi-axis optical elements, along with one or more separate slow axis optical elements and one or more separate fast axis optical elements; or any other combination thereof.

Further, each of fast axis optics 144 and slow axis optics 146 may be separate from, or integral with, scanning system 142. In other words, scanning system 142 may influence either one, both, or neither of the fast axis and slow axis intensity profiles. Thus, for example, scanning system 142 may provide fast axis optics 144, with slow axis optics 146 being provided separately. Alternatively, scanning system 142 may provide slow axis optics 146, with fast axis optics 144 being provided separately. Alternatively, scanning system 142 may provide both fast axis optics 144 and slow axis optics 146. In the example embodiment shown in FIGS. 11A-11B, slow axis optics 146 are provided by scanning system 142, while fast axis optics 144 are provided separately.

The term "optics" (e.g., as used in beam treatment optics 140, fast axis beam treatment optics 144, and slow axis beam treatment optics 146) may include a single optical element or multiple optical elements. In some embodiments, device 10 includes only a single fast axis optical element and a single slow axis optical element.

Figure 11A:
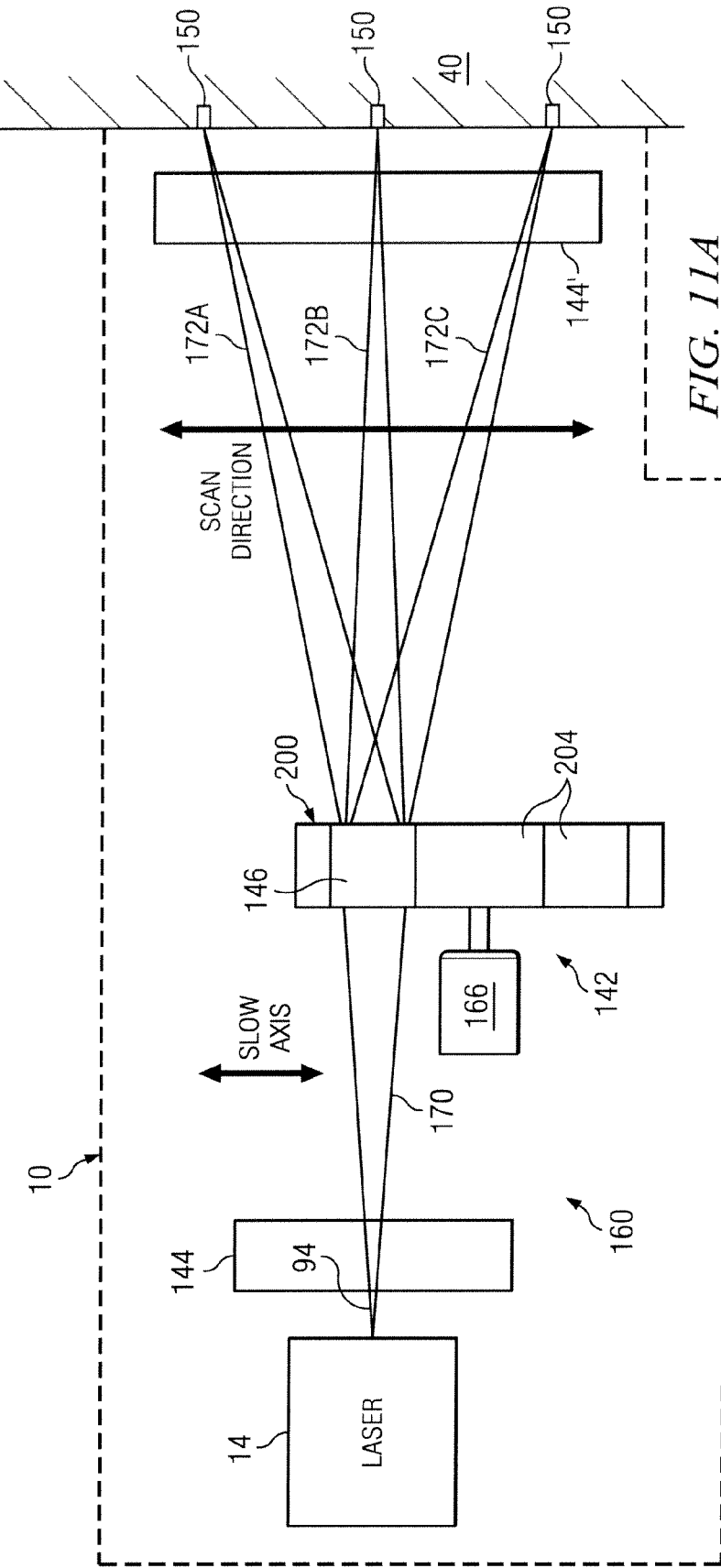

FIGS. 11A and 11B illustrate top and side views, respectively, of a beam delivery system 160 that includes a rotating scanning element 200, according to certain embodiments. Beam delivery system 160 includes a laser diode 14 that generates a beam, and optics 16 which control and scan the beam to a target area 40 to form a pattern of treatment spots 150. Optics 16 may include a fast axis optic 144, and a scanning system 142 that includes a scanning element 200 rotated by a motor 166. In some embodiments, optics 16 may also include a downstream fast axis optic 144', e.g., to refocus the fast-axis profile from a dual-beamlet profile to a single-beam profile. In other embodiments, the downstream fast axis optic 144' is omitted.

Fast axis optic 144, e.g., a rod lens, aspheric lens, or any other suitable optical element, is configured to convert the beam in the fast axis from rapidly diverging to less diverging (e.g., slowly diverging, collimated, or converging) toward target area 40, as shown in FIG. 11B. In some embodiments, fast axis lens 64 does not influence the slow axis beam angular distribution profile (e.g., the convergence/divergence of the slow axis), as shown in FIG. 11A.

Fast axis optic 144 delivers an input beam 170 to rotating scanning element 200, which includes multiple lenslets 164 that generate a successive series of output beam 172 toward target area 40, as shown in FIG. 11A. In addition to deflecting the various output beams in the scan direction to form a desired pattern of treatment spots on the target area 40, lenslets 164 of element 200 also convert the beam in the slow axis from slowly diverging to slowly converging. Thus, a single element 200 operates as both the beam scanning element and the slow axis optic 146, thus reducing or minimizing the number of separate components for such functions, which may be desirable. In some embodiments, lenslets 164 of element 200 do not influence the fast axis beam angular distribution profile (e.g., the convergence/divergence of the fast axis), as shown in FIG. 11B.

Fast axis optic 144 and lenslets 164 of element 200 may be configured to converge the beam in the fast and slow axes, respectively, such that each output beam 172 has a focal point or focal plane (i.e., target image beam spot) located at or slightly above the surface of the skin, in some embodiments. Further, as discussed above, in some embodiments a downstream fast axis optic 144' is provided for additional focusing and/or imaging and/or treatment of output beams 172.

Operation of Scanning System

FIG. 12 illustrates an example pattern 174 of treatment spots 150 (i.e., a row) delivered by one scan of a light beam by scanning system 142, with device 10 held stationary on the skin. In this example, scanning system 142 delivers 12 treatment spots to the target area 40 in a single scan of the light beam.

As discussed above, device 10 may be configured to be used in a "gliding mode," in which the device is manually dragged or glided across the skin while delivering scanned radiation to the target area 40. Scanning system 142 may repeatedly scan rows of treatment spots onto the target area 40 as device 10 is glided across the skin, thus producing a generally two-dimensional array of treatment spots on the target area 40.

In other embodiments, device 10 may be configured to be used in a "stamping mode" in which device 10 is held relatively stationary at different locations on the skin, with one or more scanned rows or arrays of treatment spots (overlapping or not overlapping) delivered at each location of device 10. Thus, device 10 may be positioned at a first location, one or more scanned rows or arrays of treatment spots may then be delivered to the skin while device 10 is held relatively stationary, device 10 may then be moved—by lifting device 10 and repositioning it or by gliding device 10 across the surface of the skin—to a new location, one or more scanned rows or arrays of treatment spots may then be delivered at that location, and so on, in order to cover a target area 40 as desired. In still another embodiment, device 10 is configured with a scanner system that provides a generally two-dimensional array relative to the device housing. For example, the scanner may include a first rotating element that scans the beam in one direction and a second rotating element that scans the beam in the orthogonal direction. As another example, a single rotating element can be can be configured to provide multiple scanned rows of output beams, as discussed below.

In other embodiments, device 10 may be configured for use in both a "gliding mode" and "stamping mode," as selected by the user, for example.

Figure 13:
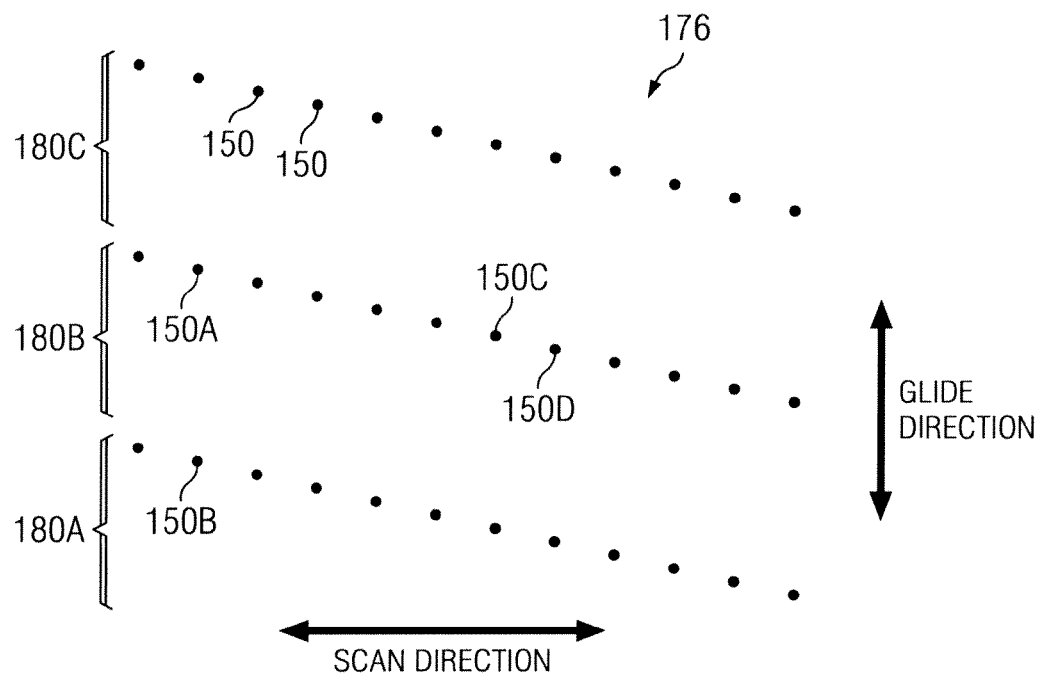
FIG. 13 illustrates an example array of treatment spots generated by the device in a gliding mode of the device.

FIG. 13 illustrates an example array 176 of treatment spots generated by device 10 used in a gliding mode. In particular, the figure shows three scanned rows of treatment spots 150, indicated as rows 180A, 180B, and 180C, aligned in the glide direction, which forms a two-dimensional array 182 of treatment spots 150. Each row 180 is generally aligned diagonal with respect to the scan direction due to the movement of the device in the glide direction during the successive delivery of individual treatment spots 150 in each row 180.

The degree to which each row is aligned diagonal with respect to the scan direction, which may influence the spacing of adjacent treatment spots aligned in the glide direction (e.g., treatment spots 150A and 150B), is a factor of multiple variables, including the device glide speed (i.e., the speed at which device 10 is glided across the skin) and the scanning rate (i.e., the rate at which treatment spots are successively delivered to the skin and the time between scans. In some embodiments, the scanning rate or particular aspects of the scanning rate (e.g., pulse on time, pulse off time, pulse frequency, etc.) may be selectable or adjustable automatically by control system 18, manually by a user, or both.

Further, the distance between adjacent treatment spots in the scan direction (e.g., treatment spots 150C and 150D) is a factor of multiple variables, including the scanning rate, distance between the center points of adjacent treatment spots, and the size and shape of individual treatment spots, which variables may be defined by the configuration of the optics of scanning system 142 or other factors. In some embodiments, one or both of these variables may be selectable or adjustable automatically by control system 18, manually by a user, or both. In some embodiments or device settings, adjacent treatment spots in the scan direction are spaced apart from each other, thus providing fractional treatment. In some embodiments or device settings, adjacent treatment spots in the scan direction may abut each other edge-to-edge, or may overlap each other, in order to provide contiguous rows of irradiated areas. Such contiguous rows may be spaced apart from each other in the glide direction, may abut each other edge-to-edge, or may overlap each other to provide a fully covered (i.e., non-fractional) irradiated area, as defined by a variety of factors such as those discussed above, which may or may not be manually and/or automatically selectable or adjustable.

Thus, it should be clear that the fractional pattern of treatment spots shown in FIG. 13, in which treatment spots are spaced apart from each other in both the glide direction and scan direction, is merely one example pattern. Device 10, and in particular scanning system 142, may be configured to provide a wide variety of treatment spot patterns.

Scanning system 142 may include any suitable optics and other elements for scanning an individual light beam into a sequentially-delivered array of beams to form a pattern of treatment spots on the target area 40. For example, as discussed below, scanning system 142 may include a rotating element having a number of deflection sectors that successively deflect (e.g., reflect or transmit with a deflection) a single incident light beam to provide an array of successively delivered output beams. In some embodiments, the rotating element may be generally disc-shaped, or generally cup-shaped, for example. The deflection sectors may be arranged around a circumference of the rotating element and may be configured to successively deflect the incident light beam by different angles to provide a successive array of deflected output beams. This array of deflected output beams may be delivered directly to the target area 40, or may be influenced by further optics before being delivered to the target area 40. For example, optics may be provided to parallelize the array of deflected beams before being delivered to the target area 40.

Figure 14:
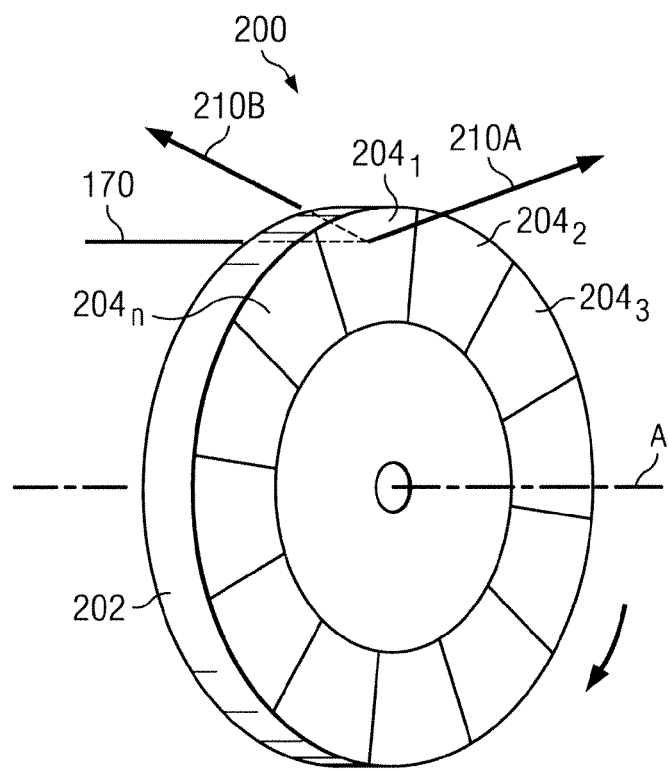
FIG. 14 illustrates a basic structure of an example rotating element for a beam-scanning system, according to some embodiments.

FIG. 14 illustrates a basic structure of rotating element 200, according to some embodiments. Element 200 has a body 202 configured to rotate about an axis A. Body 202 includes a plurality of sectors 204 generally arranged around the circumference or periphery of the body 202 and configured to deflect an input beam 170 into an array of output beams 172 offset from each other. Depending on the particular embodiment, each sector 204 may transmit but deflect the input beam 170, as indicated by example arrow 210A (e.g., a transmissive element) or reflect the input beam, as indicated by example arrow 210B (e.g., a reflective element). As each individual sector 204 rotates through the input beam 170, the deflection of the corresponding output beam 172 may remain constant or near constant so that each output beam 172 is stationary or near stationary with respect to device 10. Alternatively, the deflection of each output beam 172 may vary during the rotation of the corresponding sector 204 through the input beam 170 so that each output beam 172 traces a pattern, such as a line or arc.

Also, in addition to deflecting an input beam 170 to generate an array of offset output beams 172 (e.g., offset along a scan direction), each sector 204 may further influence the input beam 170 in one or more axis. For example, each sector 204 may further influence the input beam 170 by having curvature in its reflection surface that provides optical power, similar to the examples provided above for the transmissive disk or cup shaped scanning elements. For example, in addition to the deflection, each sector 204 may further act as a slow axis optic and/ora fast axis optic. In some embodiments, each sector 204 may deflect the input beam 170 in the slow axis direction, and also influence the convergence/divergence of the input beam 170. For example, element 200 may receive an input beam 170 that is diverging in the slow axis direction, and each sector 204 may both (a) deflect the input beam 170 by a particular degree, and (b) convert the diverging beam into a collimated or converging beam, e.g., such that individual collimated, focused, or pseudo-focused output beams 172 can be delivered to the target area, for generating treatment spots.

In addition to the various aspects of element 200 and sectors 204 discussed above, in some embodiments, individual sectors 204 may be configured to produce output beams 172 having a constant angular deflection as that sector 204 rotates through the input beam 170.

Each sector 204 (or least some of the sectors 204) may be a "constant angular deflection" sector, which is defined a sector that deflects the input beam 170 such that the angular deflection of the output beam 172 relative to the input beam 170 remains substantially constant as that sector 204 rotates through the input beam 170. In other words, the angular direction of each output beam 172 remains substantially constant relative to the input beam 170 (and relative to the structure of device 10) during the time that each corresponding sector 204 rotates through the input beam 170. Some elements 200 generate an array of constant angular deflection output beams 172 that propagate at constant angles that are different from each other.

Thus, with constant angular deflection sectors 204, if device 10 is held stationary relative to the user's skin, each output beam 172 will substantially dwell at a particular point on target area 40 until the next successive sector 204 rotates into the path of the input beam 170, at which time the beam "jumps" to a new location corresponding to the next successive output beam 172. Thus, if device 10 is held stationary relative to the user's skin, constant angular deflection sectors 204 provide substantially stationary treatment spots on the skin.

However, as discussed above, in at least some embodiments or operational modes, device 10 is designed to be glided across the surface of the skin during operation, in a manner similar to a shaver being glided across the skin. Thus, in a system with constant angular deflection sectors 204, each output beam 172 moves relative to the skin as device 10 glides across the skin, such that each treatment spot moves relative to the skin, resulting in elongation, "smearing," "blurring" in the direction of the gliding. However, despite this smearing of individual treatment spots, sufficient thermal energy may be provided to the treatment spots on a delivered energy per volume basis to provide the desired affect in the target area 40, at least within a range of operating parameters. For example, the desired effect may be provided as long as the device 10 is not glided across the skin extremely rapidly. Further, some amount of smearing may actually be beneficial for achieving a desired level of delivered energy per volume of irradiated or affected tissue, as a function of selected design and/or operational parameters (e.g., spot size and/or shape, beam intensity, fluence, and/or intensity profile of the delivered output beams, pulse duration and/or frequency, rotational speed of rotating element 200, etc.). Thus, in certain embodiments, "constant angular deflection" sectors may be used to achieve the desired treatment effects.

In some embodiments, smearing caused by gliding may be compensated for, either partially or entirely. For example, the sectors 204 may be configured to be (a) substantially stationary in the non-glide direction (for which there is no smearing) and (b) to move the beam in the glide direction (for which there is normally smearing) at the same rate or nearly the same rate as the gliding, thereby compensating or partially compensating for smearing. In these embodiments, a glide rate sensor may provide feedback to the user or the device to ensure that the gliding rate is within predefined ranges such that the smearing compensation is effective.

Direct Exposure Embodiments

As discussed above, some embodiments of device 10 are "direct exposure" embodiments that do not include any optics 16 downstream of laser diode 14. Due to rapid divergence of beam 94 emitted from laser diode 14, the laser diode 14 may be positioned very close to the application end (or "tip") 42 of the device that contacts the skin during treatment (and thus very close to the target surface). For example, some direct exposure devices are also configured for close proximity radiation in which the laser diode 14 is positioned such that the emitting surface 80 is less than 10 mm, less than 2 mm, or even less than 1 mm from the leading surface of the application end 42 (and thus less than 10 mm, 2 mm, 1 mm, 500 µm, 200 µm, or even 100 µm from the target surface when the application end 42 is placed in contact with the skin), as discussed above.

Some direct exposure embodiments of device 10 comprise a compact fractional skin treatment device, including one or more multi-emitter laser diodes 14 that deliver pulsed laser beams to the skin to generate treatment spots 150 in a target area 40 of skin, e.g., to treat wrinkles, pigmentation and coarse skin caused by photodamage. (The following discussed refers to a multi-emitter laser diodes 14, but it should be understood that device 10 may include multiple multi-emitter laser diodes 14). An application end 42 of the device may be manually glided across the target area 40 to create a distribution or array of treatment spots 150.

In some embodiments, the multi-emitter laser diode 14 is pulsed with a pulse rate set or selected based on a typical or expected speed at which the device is manually glided across the skin ("glide speed"). In particular, the pulse rate may be set or selected such that for a range of typical or expected manual glide speeds, adjacent treatment spots 150 are physically separated from each other by areas of non-treated skin (i.e., fractional treatment is provided). In some embodiments, the pulse rate may be set or selected such that for a range of typical or expected manual movement speeds, adjacent treatment spots 150 are physically separated from each other from a predetermined minimum non-zero distance, e.g., 500 µm.

In some embodiments, laser diode 14 may be pulsed at a rate between 0.5 and For example, laser diode 14 may be pulsed at a rate between 2 and 30 Hz. In particular embodiments, laser diode 14 may be pulsed at a rate between 10 and 20 Hz, e.g., about 15 Hz. The energy per pulse on a given treatment zone can be achieved by a single pulse or by multiple repetitive pulses. In some embodiments, the device may be controlled to prevent or reduce the incidence or likelihood of treatment spot overlap, e.g., based on feedback from one or more sensors (e.g., a dwell sensor, motion sensor, and/or displacement sensor). In some embodiments, the pulse rate may be automatically adjustable by the device and/or manually adjustable by the user, e.g., to accommodate different manual movement speeds and/or different comfort levels or pain tolerance levels of the user.

Some embodiments include other devices or techniques that individually or in combination provide over-treatment protection, e.g., to prevent pulse stacking, firing on the same area, an excessive density of treatment spots 150, or other non-desirable treatment conditions. For example, the device may cease to operate (e.g., generate beams) when stationary. A stationary condition may be measured by signal change induced by motion or lack of motion in capacitive, optical reflection, remittance, or scattering variation, acoustical reflection variation, acoustical impedance, galvanic potential, potential difference, dielectric constant variation, thermal variation, and so on.

As another example, a stationary condition may further be measured by local pyrometry. The treatment beam area is optically measured by "local thermal imaging". Local heating above a threshold indicates loss of motion. A stationary condition may further be measured by bulk heating measurement. If the tip of the treatment delivery device begins to heat above a threshold, loss of motion is detected, or excessive treatment in the area is detected.

As another example, the device may fire an "encouragement pulse" when stationary. A single non-damaging but higher than normal energy pulse or brief pulse train is emitted if the device becomes stationary to encourage the user to move on.

As another example, the device may deliver heat or cold to encourage motion. Dwelling in one place would become uncomfortable. As another example, mechanical rollers may detect a non-motion condition. Motorized rollers may drive motion physically avoiding a non-motion condition.

As yet another example, the output pulse frequency or energy may be adjusted to compensate for displacement speed reduction or cessation so as to avoid insufficient spacing of treatment spots 150, pulse stacking, or generalized overtreatment.

Some direct exposure embodiments of device 10 include a single multi-emitter laser diode 14. Other embodiments include multiple multi-emitter laser diodes 14, e.g., arranged as a laser diode bar or otherwise arranged to form a one-dimensional or two-dimensional array of laser diodes. As discussed above, the beam 94 emitted from each laser diode 14 diverges in both a fast axis and a slow axis. Thus, in such embodiments, if the device includes no optics downstream of the laser diode(s) 14, each beam 94 exits the application end of the device, and reaches the target surface as a diverging beam. As discussed below, this may provide an aspect of eye-safety. In some embodiments, the arrangement of laser diode(s) 14 and/or the divergence of the beam(s) 94 emitted from laser diode(s) 14 may provide sufficient eye safe radiation such that an eye safety sensor or system may be omitted, e.g., as discussed below.

Each laser diode 14 may be selected or configured to emit a beam of any suitable wavelength and energy level. In some embodiments, each laser diode 14 may emit a beam having a wavelength absorbed by water in the skin, e.g., a wavelength between 1400 and 2000 nm. In particular embodiments, each laser diode 14 emits a beam having a wavelength of about 1450-1550 nm±50 nm. In other embodiments, each laser diode 14 emits a beam having a wavelength of about 1926 nm±50 nm. In some embodiments that include multiple emitters, different emitters may emit light at different wavelengths. For example, a device may include one or more first laser diodes 14 that emit a wavelength of about 1450-1550 nm±50 nm and one or more second laser diodes 14 that emit a wavelength of about 1926 nm±50 nm.

In some embodiments, each laser diode 14 may emit a total energy of between about 2 mJ and about 30 mJ per beam 94 (i.e., per treatment spot 150). For example, each laser diode 14 may emit between about 5 mJ and about 15 mJ per beam 94. In particular embodiments, each laser diode 14 emits about 10 mJ per beam 94.

In some direct exposure embodiments, device 10 has an energy setting that can be optionally set to different values by a smart charging base accessory or on the device itself. Device 10 may include one or more types of sensors 26 for use in controlling the operation of the device, e.g., a skin contact sensor to detect contact with the skin, a dwell sensor to detect stationary positioning, a motion sensor to detect motion and/or speed of the device, and/or a displacement sensor configured to determine the distance (if any) that the device has moved across the skin. Any two or more of these sensors may be combined into a single sensor responsive to one or more than one parameter. Device 10 may include a single power button (mechanical or virtual) that the user activates to initiate the laser treatment. In one embodiment, once the application end of device 10 is in contact with skin and is not stationary on the skin (e.g., gliding or otherwise moving across the surface of the skin), device 10 enables the delivery of treatment laser energy as long as the power button is activated. The manual movement results in a generally random pattern of spots and a density of treatment spots 150 in the treated skin area, based on the manual movement of device 10 across the skin. The user can move device 10 across the skin at different speeds to help achieve the desired treatment comfort level. One or more sensors 26, e.g., a dwell sensor, displacement sensor, and/or motion sensor may be detect whether or not device 10 is moving, the speed of movement, and/or the distance device 10 has moved. Device 10 may utilize such detected data to prevent over-treatment of the same location on the skin.

Certain example direct exposure embodiments of device 10 are handheld, battery powered, compact fractional treatment devices with all solid-state components (e.g., no mechanical motors) providing skin area coverage via manual motion (gliding or otherwise moving) modality and a pulsed light source.

Some embodiments are configured to generate laser beams at a wavelength absorbed by water in the skin, such as a wavelength between 1400 and 2000 nm, delivered in a single beam or a row or array of beams each approx. 300 μm in equivalent nominal diameter and direct proximity exposure from one or more laser diode emitters to the skin target. For example, certain embodiments are configured to generate 1450-1550 nm+/−50 nm infrared light, delivered in a single beam or a row or array of beams each approx. 300 μm in equivalent nominal diameter and direct proximity exposure from one or more laser diode emitters to the skin target.

Figure 15:
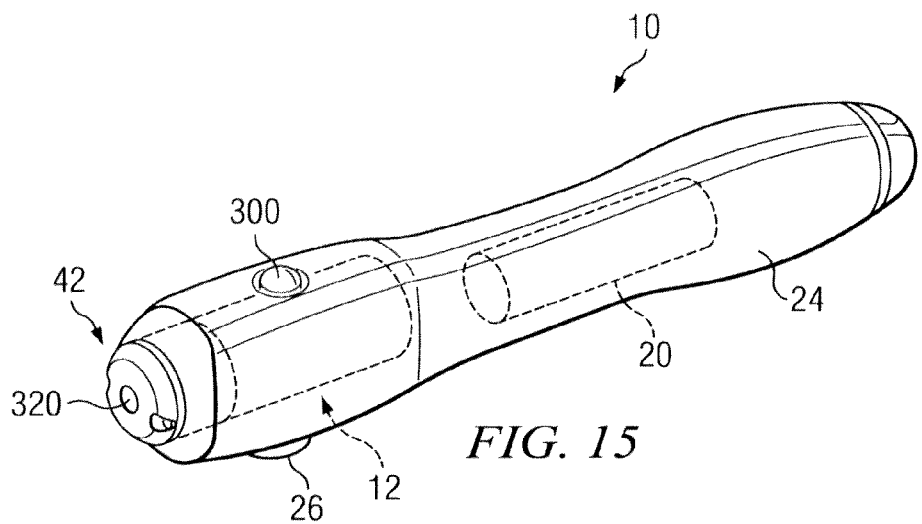
FIG. 15 illustrates an example laser-based treatment device configured as a direct exposure device for providing fractional treatment, according to certain embodiments of the present disclosure.

FIG. 15 illustrates an example device 10 configured as a direct exposure device for providing fractional treatment, according to certain embodiments of the present disclosure. The example device includes a laser engine 12 including a multi-emitter laser diodes 14 and one or more batteries 20 within a device housing 24. In some embodiments, the battery or batteries 20 may be provided in the laser engine 12. Battery or batteries 20 may include any number and type of batteries, e.g., AA-sized or smaller batteries, or rechargeable or non-rechargeable cells (e.g., Li ion cells), or any other type of battery.

Device 10 has an application end 42 configured to contact the user's skin as device 10 is moved across the skin during a treatment session. In this embodiment, application end 42 is defined by a leading end of laser engine 12, which projects from device housing 24. The application end 42 may include a laser treatment aperture through which a laser beam 96 generated by the laser engine 12 is delivered to the user. In addition, as discussed above, one or more sensors 26, e.g., a skin contact sensor, a dwell sensor, a motion sensor, and/or a displacement sensor may be located on device 10, e.g., at application end 42. In some embodiments, such sensors may include, e.g., any of the various sensors disclosed in U.S. Ser. No. 13/366,246 (e.g., one or more skin-contact sensor 104, dwell sensor 116, motion/speed sensor 102, and/or displacement sensor 100A, 100B, 100C, or 100D). In some embodiments, device 10 includes a skin contact sensor and a dwell sensor configured to avoid unintentional exposure and/or overexposure of the skin (e.g., by preventing stacking or overlapping of treatment spots 150). The skin contact sensor and dwell sensor may be provided by a single combined contact/dwell sensor, or may be provided as separate sensors. In either alternative, the sensor(s) may be optical or capacitance based or use other suitable means. Contact with the skin may be detected by analyzing an amplitude of an optical reflectance or capacitance signal generated by the sensor. Further, dwelling of device 10 on the skin may be detected by analyzing signal in the optical reflectance or capacitance signal associated with application end 42 of device 10 moving across the skin or by other suitable means. Because skin surface is not perfectly smooth and the manual moving of a device cannot achieve perfect steady motion, stiction (static friction) between device 10 and skin and/or other physical principles result in micro-displacement between the sensor and the skin surface. For example, a capacitive sensor's signal is inversely proportional to the relative displacement between the sensor and the test surface. Any micro-displacement due to stick-and-slip manual movement will result in a translational signal on top of the nominal steady-state sensor signal. This signal may be analyzed to determine whether device 10 is moving across the skin, or dwelling at the same location. Such analysis may include any suitable algorithms, e.g., comparing the signal to one or more threshold values.

In the example shown in FIG. 15, device 10 includes a power button 300. Device 10 enables the delivery of beams to the skin in a pulsed manner when power button 300 is manually depressed, and sensor(s) 26 detect that device 10 is in proper contact with the skin and moving across the skin (i.e., not dwelling on the skin).

The specific user interface scheme, and the shape and size of device 10 housing may be selected as desired. In some embodiments, the shape and size of device 10 housing is easy to grip and includes a simple, conveniently located power button 300 and/or other user interfaces. In addition, the shape of device 10 may be ergonomic, and/or be configured to provide good visibility of the target area 40.

Figure 16A:
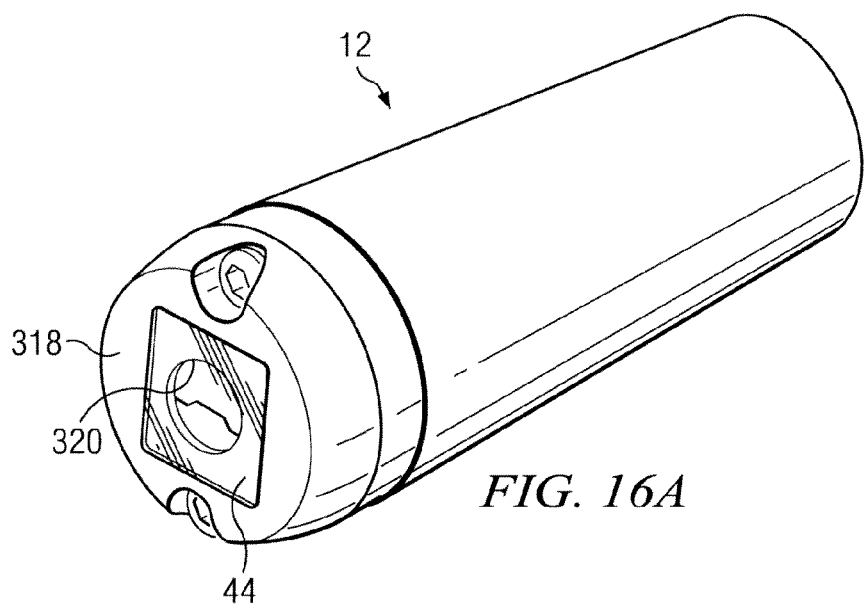
FIGS. 16A-16B illustrate an example light engine for use in the direct exposure laser treatment device shown in FIG. 15, according to an example embodiment.
Figure 16B:
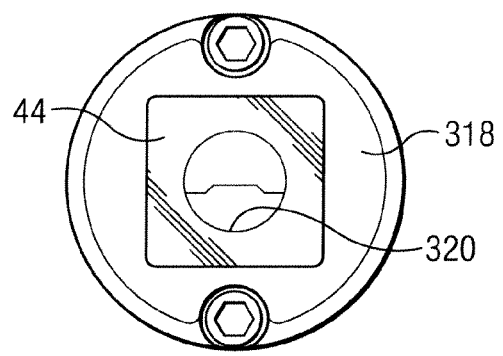
Figure 17:
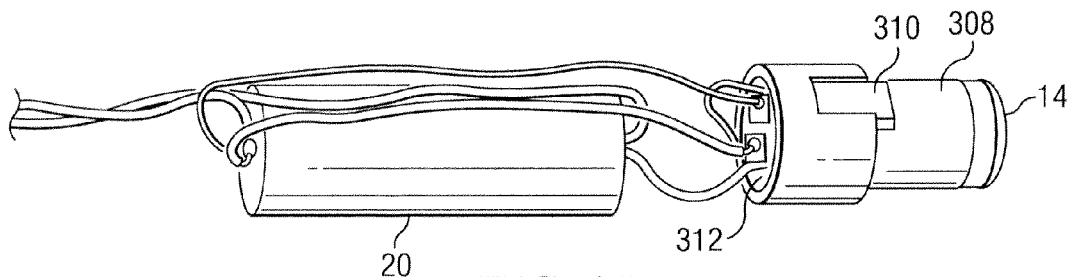
FIG. 17 illustrates an exploded view of the example light engine shown in FIG. 16.

FIGS. 16 and 17 illustrate details of an example light engine assembly 12 for use in the direct exposure fractional treatment device of FIG. 15, according to certain embodiments. In particular, FIG. 16 illustrates an assembled view of the example light engine, while FIG. 17 illustrates an exploded view of the various components of device 10.

The light engine assembly 12 may include a multi-emitter laser diode chip, mounted on a heat spreader, which is in turn mounted to a thermal reservoir heat sink 308. The laser diode 14 is powered by one or more battery 20, by way of a momentary switch 310 (activated by power button 300 shown in FIG. 15) and pulsing electronics 312, which control the pulsing of the laser diode 14. The components shown in FIG. 17 may be contained in a laser engine housing 24, which may include housing sections held together by any suitable fasteners, e.g., as shown in FIG. 16. As discussed above, other light sources, such as a laser diode bar, may be used. Furthermore, other power supply sources 20 may be used, such as mains electricity or a super-capacitor.

In some embodiments, the laser engine 12 may be comprised of one or more laser diodes 14 directly mounted to a heat sink 308 via suitable means (e.g., via soldering, clamping, or adhesive) or mounted to one or more subcarriers (e.g., a ceramic, plated ceramic, copper block, etc) to provide, among other things, electrical isolation and/or thermal conduction. Electrical connection to the laser diode(s) 14 may be made by wire bonding, clamping, or other suitable means between the laser diode(s) 14 and the subcarrier(s), to the heat sink 308, or to other electrical connection point(s) (e.g., a printed circuit board) in device 10.

In some embodiments, the heat sink 308 may also be an internal chassis for supporting components of the light engine 12. In some embodiments, the light output (power and wavelength) of the laser diode 14 may be sensitive to temperature and should be held to a predetermined maximum temperature rise (e.g., about 25° C.). Thus, the heat sink 308 may include a temperature feedback system to automatically disable the laser if the maximum temperature is exceeded.

FIG. 16 illustrates example dimensions of the light engine assembly 12 according to one embodiment. FIG. 16 also shows an example configuration of application end 42 of the light engine assembly 12, which includes a window 44 covering an aperture 320 through which the laser beam 94 is delivered from the laser diode 14 to the skin. In this embodiment, window 44 comprises a transparent layer or pane (e.g., glass or plastic) positioned over aperture 320 to protect the internal components of light engine 12. In other embodiments, aperture 320 may be open or light engine 12 may be protected by a transparent (to laser diode 14) encapsulate, such as suitable epoxy or spun-on-glass, rather than window 44. Aperture 320 may have any suitable size and shape. Light engine assembly 12 may act as application end 42 of device 10, and thus contact the skin directly. Application end 42 may also form part of one or more of the sensors 26, such as providing a capacitive antenna for a skin contact sensor. Window 44 may project beyond an outer surface 318 of application end 42, may be arranged flush with outer surface 318 of application end 42, or may be slightly recessed from outer surface 318 of application end 42.

In some embodiments, the laser diode chip 14, and in particular the emitting surface 80 of laser diode 14, is configured to be located very close to the target skin surface, and there are no optics between the laser and the treatment target plane. As discussed above, a (non-optically-powered) transparent layer or pane, or encapsulant, may be positioned between the laser diode 14 and the target surface, or there may be nothing but an air gap between the laser diode 14 and the target surface. In some embodiments, the emitting surface 80 of laser diode 14 is configured to be located within 10 mm of the target skin surface, to provide a desired beam spot size and intensity at the target surface. For example, the emitting surface 80 of laser diode 14 may be configured to be located within 5 mm of the target skin surface. In certain embodiments, the emitting surface 80 of laser diode 14 is configured to be located within 2 mm of the target skin surface, to provide a desired beam spot size and intensity at the target surface. In particular embodiments, the emitting surface 80 of laser diode 14 is configured to be located within about 1 mm of the target skin surface. Still further, in some embodiments, the emitting surface 80 of laser diode 14 is positioned less than 500 µm, 200 µm, or even 100 µm from the target skin surface Due to the very small distance between the laser diode 14 and the target skin surface and/or lack of optics, the laser diode 14 need not be aligned with high precision.

In some embodiments, various aspects of device 10 (the distance between multi-emitter laser diode 14 and the skin surface, etc.) are configured to produce treatment spots 150 on the skin having a diameter of less than 2,000 µm in the largest dimension. In particular embodiments, the beam spot size on the target surface has a diameter of less than 700 µm in the largest dimension, which may be suitable for certain treatments, e.g., treatment of solar lentigo (age spots), wrinkles, and/or fine lines. In specific embodiments, the beam spot size on the target surface has a diameter of between about 75 µm and about 350 µm in the largest dimension, which may be suitable for certain treatments, e.g., treatment of wrinkle and/or fine lines. The diameters listed above do not account for any "blurring" or "smearing" of the treatment spots 150 caused by movement of device 10 across the skin during the particular beam pulse. The actual diameter of particular treatment spots 150 (in the direction of device 10 movement across the skin) may thus be larger than the nominal diameters listed herein, due to such blurring or smearing of spots 150.

In some embodiments, device 10 is configured to produce treatment spots 150 having an area of less than 1.0 mm$^2$. In particular embodiments, device 10 is configured to produce treatment spots 150 having an area of less than 0.4 mm$^2$, which may be suitable for certain treatments, e.g., treatment of solar lentigo (age spots), wrinkles, and/or fine lines. In specific embodiments, device 10 is configured to produce treatment spots 150 having an area of less than 0.1 mm$^2$, which may be suitable for certain treatments, e.g., treatment of wrinkle and/or fine lines or pigmentation. Finally, in some embodiments, device 10 is configured to produce treatment spots 150 having an area of less than 0.05 mm$^2$, which may also be suitable for certain fractional treatments. The treatment size areas listed above do not account for any "blurring" or "smearing" of the treatment spots 150 caused by movement of device 10 across the skin during the particular beam pulse. Thus, the actual area of individual treatment spots 150 may be larger than the areas listed above, due to such blurring or smearing of spots 150.

In one example embodiment, device 10 employs a dual-emitter laser diode 14 in which each of the two emitters has a nominal laser emitter area of about 100 µm (in the slow axis direction) by 1 µm (in the fast axis direction), with the two emitters spaced apart in the fast axis direction by about 5 µm, and wherein the emitting surface of laser diode 14 is positioned less than 1 mm from the target skin surface. This configuration may yield treatment spots 62 having an equivalent nominal diameter of between about 150 µm and about 350 µm.

It should be understood that device 10 may include one or more multi-emitter laser diode 14 configured in any suitable manner with respect to the application end 42 of device 10. For example, device 10 may include one or more multi-emitter laser diode 14 arranged in any of the various configurations and with any of the various example dimensions (e.g., window thickness ($T_W$), gap distance ($D_G$), and proximity gap spacing (PGS)) shown in and discussed with reference to FIGS. 10-16 of U.S. Ser. No. 13/366,246, e.g., for providing treatment spots of desired shapes and sizes as discussed therein.

Figure 18:
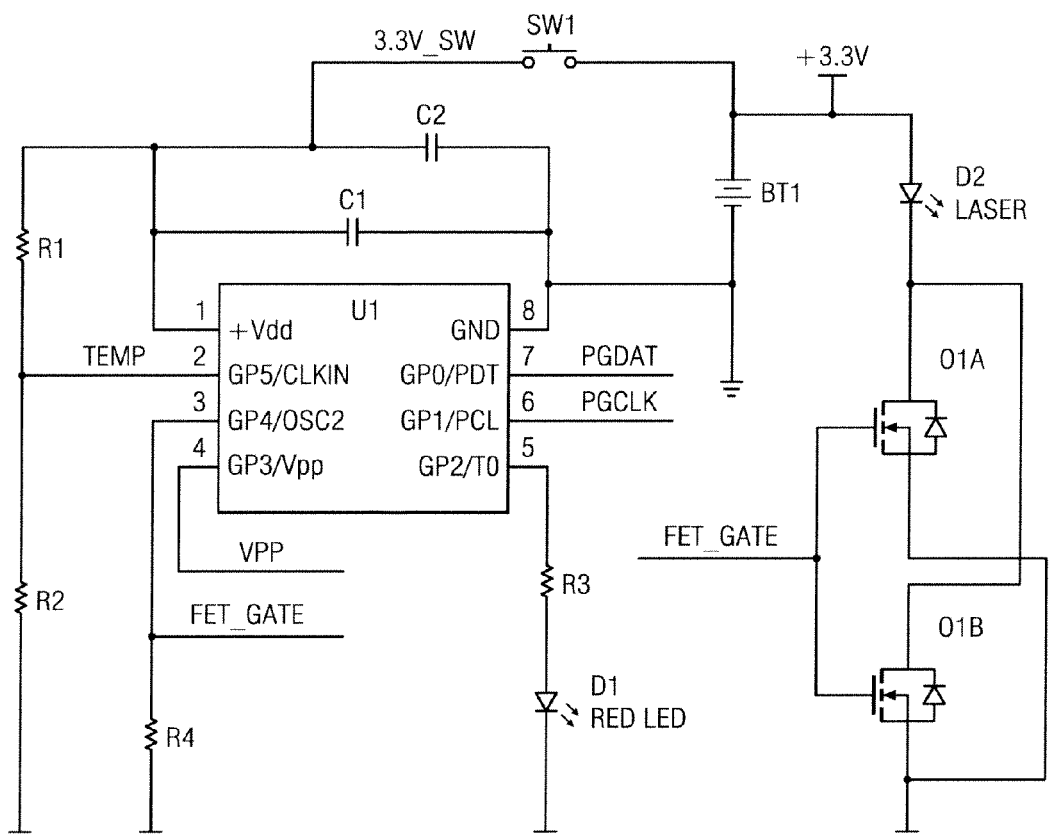
FIG. 18 illustrates an example electrical schematic of laser pulsing electronics for controlling the pulsing of the laser diode of the example direct exposure laser treatment device shown in FIGS. 15-17.

FIG. 18 illustrates an example electrical schematic of the laser pulsing electronics 312 for controlling the pulsing the laser diode 14 of the example embodiment shown in FIGS. 15-17, according to one embodiment. In this embodiment, the laser pulsing electronics 312 generate current pulses through the laser diode 14 at a fixed rate as long as the contact/dwell sensor signal is valid and the manual power button 300 is activated. The pulse energy may be controlled via the pulse duration. A single-cell AA-sized Li battery may be used to provide a drive current of about 5 A through the laser diode, to provide a laser output power of about 3 W, sufficient to produce desired tissue response for particular applications.

As discussed above, the pulse rate may be set or selected based on a typical or expected speed at which device 10 is manually glided across the skin ("glide speed"). In particular, the pulse rate may be set or selected such that for a range of typical or expected glide speeds, adjacent treatment spots 150 are physically separated from each other by areas of non-treated skin (i.e., fractional treatment is provided). In some embodiments, device 10 may be controlled to prevent or reduce the incidence or likelihood of treatment spot overlap, e.g., based on feedback from one or more sensors 26 (e.g., a dwell sensor, motion sensor, and/or displacement sensor). In some embodiments, the pulse rate may be automatically adjustable by device 10 and/or manually adjustable by the user, e.g., to accommodate different manual movement speeds and/or different comfort levels or pain tolerance levels of the user.

Eye Safety

Some embodiments of device 10 provide eye safe radiation, by delivering a substantially divergent beam 94 from multi-emitter laser diode 14 (e.g., with no downstream optics), and/or using an eye safety control system including one or more sensors 26, and/or by any other suitable manner. For example, in some embodiments or settings (including certain direct exposure embodiments and certain indirect exposure embodiments), device 10 meets the Class 1M or better (such as Class 1) eye safety classification per the IEC 60825-1, referred to herein as "Level 1 eye safety" for convenience. In other embodiments or settings (including certain direct exposure embodiments and certain indirect exposure embodiments), the device exceeds the relevant Maximum Permissible Exposure (MPE) (for 700-1050 nm wavelength radiation) or Accessible Emission Limit (AEL) (for 1400-1500 nm or 1800-2600 nm wavelength radiation) by less than 50%, referred to herein as "Level 2 eye safety" for convenience. In still other embodiments or settings (including certain direct exposure embodiments and certain indirect exposure embodiments), the device exceeds the relevant MPE (for 700-1050 nm wavelength radiation) or AEL (for 1400-1500 nm or 1800-2600 nm wavelength radiation) by less than 100%, referred to herein as "Level 3 eye safety" for convenience. The Accessible Emission Limit (AEL), as specified in IEC 60825-1, e.g., for 700-1050 nm wavelength radiation, is discussed below. Maximum Permissible Exposure (MPE), which is relevant, e.g., for 700-1050 nm wavelength radiation, is not discussed below but is specified in IEC 60825-1: 2007. In other embodiments or settings (including certain direct exposure embodiments and certain indirect exposure embodiments), device 10 meets the next highest eye safety classification after Class 1M per the IEC 60825-1, i.e., Class 3B, referred to herein as "Level 4 eye safety" for convenience.

Some embodiments of device 10 configured for direct exposure (and/or close proximity exposure) of laser radiation provide Level 4 eye safety as defined above; some direct exposure embodiments provide Level 3 eye safety as defined above; some direct exposure embodiments provide Level 2 eye safety as defined above; and some direct exposure embodiments provide Level 1 eye safety as defined above. Some embodiments of device 10 configured for indirect exposure (and/or close proximity exposure) of laser radiation provide Level 4 eye safety as defined above; some direct exposure embodiments provide Level 3 eye safety as defined above; some direct exposure embodiments provide Level 2 eye safety as defined above; and some direct exposure embodiments provide Level 1 eye safety as defined above.

Such levels of eye safety may be provided based on a combination of factors, including for example, one or more of the following: (a) the divergence of the beam(s), (b) the emitted power, (c) the wavelength of the emitted beam(s), (d) the arrangement of the multi-emitter laser diode(s), and in pulsed radiation embodiments or applications of device 10: (e) the pulse duration, and (f) the total energy per pulse. Thus, in some embodiments (including certain direct exposure, close proximity embodiments; certain direct exposure, remote proximity embodiments; certain indirect exposure, close proximity embodiments; and certain indirect exposure, remote proximity embodiments), one, some, or all of such factors may be selected or adjusted to provide Level 1, Level 2, Level 3, or Level 4 eye safety, as defined above.

In some embodiments, the extent of the beam divergence from a multi-emitter laser diode provides an eye safety aspect. For example, the beam divergence from a multi-emitter laser diode (in both the fast axis and slow axis) may provide Level 1, Level 2, Level 3, or Level 4 eye safety, depending on the other selected parameters. An analysis of relevant issues is discussed below. It should be noted that the eye safety analysis, at least with respect to the IEC 60825-1 standards, for a multi-emitter laser diode is essentially the same as the analysis for a single-emitter edge-emitting laser diode, as they have essentially the same far-field angular distribution profile.

In the wavelength ranges of 1400-1500 nm and 1800-2600 nm (e.g., for providing certain fractional treatments), corneal damage is typically the primary concern for eye safety. In some embodiments that radiate in such wavelength ranges, the beam divergence inherently provided by the multi-emitter laser diode, alone or in combination with other eye safety features, may provide a desired eye safety for device 10. For example, the beam divergence from a multi-emitter laser diode (alone or in combination with other eye safety features) may provide Level 1, Level 2, Level 3, or Level 4 eye safety, depending on the other selected parameters. An analysis of relevant issues is discussed below.

A highly divergent intense light source may provide eye safe radiation. For certain wavelengths greater than 1400 nm (including, e.g., typical wavelengths used in fractional laser treatment), the light source is greatly attenuated by the water absorption in the eye anterior chamber. Thus, there is substantially little or no retinal hazard in this wavelength range. The emission limit is determined by the potential corneal damage. For Class 1M eye safety classification per IEC 60825-1, the Accessible Emission Limit (AEL) in the wavelength range of 1400 to 1500 nm and 1800 to 2600 nm is described by a simple equation in Table 4 of IEC 60825-1:2007:

$$AEL = 4.4 t^{0.25} \text{ mJ} \qquad \text{Equation 1}$$

AEL energy is measured at 70 mm from the source with a circular aperture of 7 mm in diameter (Condition 2 measurement setup described in Table 11 of IEC 60825-1:2007, applicable for diverging beam). In this equation, t (in unit of seconds) is the source pulse duration in the range of 1 ms to 350 ms. For example embodiments that include a single multi-emitter laser diode, this pulse duration may be in the range of 1 to 10 ms. The corresponding AEL is 0.8 to 1.4 mJ.

The actual source AE (Accessible Energy) can be estimated for a given beam divergent characteristics. It can also be measured experimentally with the appropriate aperture stop (7-mm wide) and measurement distance (70-mm from the source). The AE at a distance 70-mm from the treatment aperture is given by (this is approximately correct for a Gaussian beam from a diffraction limited laser):

$$AE = 2.5 \times 10^{-3} Q / [\tan(\Phi_F/2) \tan(\Phi_S/2)] \text{ mJ} \qquad \text{Equation 2}$$

where Q (in unit of mJ) is the source energy at the treatment plane, and $\Phi_F$ and $\Phi_S$ are the beam divergence in the fast and slow axis, respectively. To achieve the Class 1M eye safety classification, AE must be lower than the AEL for the corresponding pulse duration.

Table 1 below provides several example configurations and device settings for providing Level 1 eye safety (Class 1M or better per standard IEC 60825-1) for certain embodiments of device 10 that provide pulsed radiation in the 1400-1500 nm or 1800-2600 nm wavelength ranges (e.g., for fractional treatment) using a multi-emitter laser diode 14:

TABLE 1

| Parameter | Example Embodiment 1 | Specific Example of Embodiment 1 | Example Embodiment 2 | Specific Example of Embodiment 2 |
|---|---|---|---|---|
| Configuration | direct exposure (no optics) | direct exposure (no optics) | indirect exposure (with optic) | indirect exposure (with optic) |
| Radiation source | multi-emitter laser diode | multi-emitter laser diode | multi-emitter laser diode w/collimating optics | multi-emitter laser diode w/ collimating optics |
| Radiation mode | Pulsed | Pulsed | Pulsed | Pulsed |
| wavelength | 1400-1500 nm or 1800-2600 nm | 1400-1500 nm or 1800-2600 nm | 1400-1500 nm or 1800-2600 nm | 1400-1500 nm or 1800-2600 nm |
| beam divergence at skin surface | 35°-45° fast axis, 6°-12° slow | 45° fast axis 10° slow axis | 2°-12° fast axis, 6°-12° slow | 12° fast axis 12° slow axis |

TABLE 1-continued

| Parameter | Example Embodiment 1 | Specific Example of Embodiment 1 | Example Embodiment 2 | Specific Example of Embodiment 2 |
|---|---|---|---|---|
| (fast axis, slow axis) | axis | | axis | |
| Pulse duration (ms) | 1-8 | about 3 | 1-15 | about 5 |
| Power (W) | 2-6 | about 4 | 1-4 | about 1 |
| Total energy per pulse (mJ) | 5-15 | about 12 | 5-15 | about 5 |
| AEL (mJ) | 0.8-1.3 | about 1.0 | 0.8-1.5 | about 1.2 |
| AE (mJ) | 0.3-2.3 | about 0.8 | 1.1-41 | about 1.1 |
| Eye safety classification | Class 1M for AE < AEL | Class 1M | Class 1M for AE < AEL | Class 1M |

Because certain embodiments or device settings may provide Level 1, Level 2, Level 3, or Level 4 eye safety based on the appropriate selection of parameters discussed above, in some such embodiments an eye safety sensor or system may be omitted. However, some such embodiments, even those providing Level 1 eye safety, may include an eye safety sensor or system to provide redundancy, to meet particular regulatory standards, or for other reasons.

In at least some embodiments additional eye safety is provided by incorporating a contact sensor that enables pulsing of the light source only when in contact with the skin. Thus, in such embodiments, the likelihood of corneal eye injury may be reduced or substantially eliminated unless the device is literally pressed to the eye surface.

Some embodiments may include an optical diffuser or radiation-diffusing elements or configuration (e.g., as described in U.S. Pat. No. 7,250,045, U.S. Pat. No. 7,452,356, or US Patent Application Publication No. US 2006/0009749, all three of which disclosures are hereby incorporated by reference in their entirety), one or more optics (e.g., a lens), or other elements and configurations (e.g., selected pulse durations, wavelengths, pulse repetition frequencies, beam profile characteristics, and beam propagation characteristics) to provide increased eye safety. Other embodiments may provide a particular eye safety level (e.g., Level 1, Level 2, Level 3, or Level 4 as defined above) without such elements, and in a direct exposure configuration (and/or close proximity configuration), due to the beam divergence provided by the multi-emitter laser diode combined with suitable operational parameters of the multi-emitter laser diode, e.g., as discussed above.

The invention claimed is:

1. A dermatological treatment device, comprising:
a device body configured to be handheld;
an application end configured to be in contact with or proximate the skin during a treatment session;
a laser control circuit housed in the device body and configured to generate laser radiation for delivery to a target area of tissue, the circuit comprising:
a multi-quantum well (MQW) laser diode including a monolithic stack of layers formed on a substrate, the monolithic stack of layers including a multiple-emitter region defining at least two emitter junctions connected in electrical series and aligned along a fast-axis direction of the emitter junctions, each emitter junction configured to emit a laser beam; and
a battery source that provides current to the laser diode such that each of the at least two emitter junctions concurrently emits a laser beam, the at least two concurrently emitted laser beams at least partially combining or interacting to form a collective beam having a beam profile including a fast-axis beam profile shape that defines multiple spaced-apart intensity peaks corresponding to the multiple emitter junctions of the MQW laser diode; and
a downstream optical element arranged downstream of the laser diode and proximate the application end of the device, wherein the downstream optical element is configured to:
receive the collective beam, the fast-axis beam profile shape of the received collective beam defining multiple spaced-apart intensity peaks;
output the collective beam, the fast-axis beam profile shape of the output collective beam defining multiple spaced-apart intensity peaks; and
optically influence the beam profile of the collective beam such that, downstream of the downstream optical element, the fast-axis beam profile shape of the output collective beam changes from a first profile shape defining multiple spaced-apart intensity peaks to a second profile shape defining a single intensity peak;
wherein the device is configured for delivering the output collective beam with the second profile shape defining a single intensity peak to the target area of tissue to provide a contiguous treatment spot on the tissue for providing a fractional dermatological treatment.

2. The dermatological treatment device according to claim 1, wherein the multiple-emitter region of the laser diode defines exactly two emitter junctions.

3. The dermatological treatment device according to claim 1, wherein the multiple-emitter region of the laser diode defines at least three emitter junctions.

4. The dermatological treatment device according to claim 1, wherein the downstream optical element does not substantially influence a slow-axis beam profile shape of the collective beam.

5. The dermatological treatment device according to claim 1, wherein:
the multiple-emitter region of the laser diode is formed from at least one indium gallium arsenide phosphide (InGaAsP) or aluminum gallium indium arsenide (AlGaInAs) composition; and
the multiple-emitter region of the laser diode is formed between a p-doped cladding region and an n-doped cladding region, the p-doped cladding region and an n-doped cladding region being formed from at least one indium phosphide (InP) composition.

6. The dermatological treatment device according to claim 1, wherein the battery source is a lithium based cell.

7. The dermatological treatment device according to claim 1, wherein:
the battery source has a nominal voltage; and
the laser control circuit powers the laser diode such that a forward voltage drop of the laser diode is at least 50% of the nominal voltage of the battery source.

8. The dermatological treatment device according to claim 7, wherein:
the nominal voltage of the battery source is between 2.8V and 3.8V; and
the laser control circuit powers the laser diode such that a forward voltage drop of the laser diode is at least 1.8V.

9. The dermatological treatment device according to claim 1, wherein:
the laser control circuit provides a fixed drive current of between 1 A and 6 A to the laser diode;
the output power of the laser diode is between 0.5 W and 3.1 W; and
the voltage drop of the laser diode is between 1.9V and 2.6V.

10. The dermatological treatment device according to claim 1, wherein:
the laser control circuit provides a fixed drive current of between −3 A and −5 A to the laser diode; and
the output power of the laser diode is between 2.15 W and 3.0 W; and
the voltage drop of the laser diode is between 1.9V and 2.6V.

11. The dermatological treatment device according to claim 1, wherein the downstream optical element substantially influences a slow-axis beam profile shape in addition to the fast-axis beam profile shape of the collective beam.

12. The dermatological treatment device according to claim 1, wherein the laser diode emits radiation at a wavelength of between 1400 nm and 2000 nm.

13. The dermatological treatment device according to claim 1, wherein the laser diode emits radiation at a wavelength of between 1400 nm and 1550 nm.

14. The dermatological treatment device according to claim 1, comprising more than one multiple-emitter laser diodes.

15. The dermatological treatment device according to claim 1, wherein the laser control circuit controls the laser diode to emit pulsed laser beams.

16. The dermatological treatment device according to claim 1, wherein the laser control circuit controls the laser diode to emit continuous wave (CW) radiation.

17. The dermatological treatment device according to claim 1, wherein the device is configured to sequentially deliver a series of collective beams to the skin to generate treatment spots on the skin spaced apart from each other by areas of non-irradiated skin between the adjacent treatment spots, to provide a fractional treatment to the tissue.

18. The dermatological treatment device according to claim 1, wherein:
the device further includes:
a fast axis optical element proximate the laser diode and upstream from the downstream optical element and configured to reduce the divergence of the collective beam in the fast axis.

19. The dermatological treatment device according to claim 1, wherein the downstream optical element is a cylindrical lens located proximate the application end of the device.

20. The dermatological treatment device according to claim 1, further comprising:
a beam scanning system arranged downstream of the laser diode, the beam scanning system configured to scan the collective beam to form a pattern of treatment spots on the skin spaced apart from each other by areas of non-irradiated skin between the adjacent treatment spots, to provide a fractional treatment to the tissue.

21. The dermatological treatment device according to claim 20, wherein the beam scanning system includes a rotating element having a plurality of deflection sectors, each deflection sector configured to provide a deflected beam as that deflection sector rotates through the collective beam, the deflected beams being offset from each other to form the pattern of treatment spots on the skin.

22. The dermatological treatment device according to claim 20, wherein:
the device further includes:
an additional downstream optical element proximate the laser diode and upstream from the beam scanning system and configured to reduce the divergence of the collective beam in the fast axis.

23. The dermatological treatment device according to claim 1, wherein
the device body includes an application end configured to be moved across the surface of the skin during treatment; and
the laser control circuit further includes electronics configured to pulse the laser diode to sequentially deliver a series of collective beams to the skin to generate treatment spots on the skin during movement of the application end across the surface of the skin, such that adjacent treatment spots generated on the skin are spaced apart from each other by areas of non-treated skin between the adjacent treatment spots.

24. The dermatological treatment device according to claim 1, wherein the collective beam is divergent in the at least one direction upon incidence with the skin surface.

25. The dermatological treatment device according to claim 1, wherein:
the device body includes an application end configured to be in contact with the skin during delivery of the laser radiation; and
the laser diode is arranged such that when the application end is in contact with the skin, an emitting surface of the laser diode from which the laser beams are emitted is spaced from the skin surface by less than 10 mm.

26. The dermatological treatment device according to claim 1, wherein:
the device body includes an application end configured to be in contact with the skin during delivery of the laser radiation; and
the laser diode is arranged such that when the application end is in contact with the skin, an emitting surface of the laser diode from which the laser beams are emitted is spaced from the skin surface by less than 2 mm.

27. The dermatological treatment device according to claim 1, wherein the device is fully solid-state with no automated moving components.

28. A method for providing a dermatological treatment, comprising:
providing a handheld device including a laser control circuit comprising:
a multi-quantum well (MQW) multiple-emitter laser diode including a monolithic stack of layers formed on a substrate, the monolithic stack of layers including a multiple-emitter region defining at least two emitter junctions connected in electrical series and aligned along a fast-axis direction of the emitter junctions, each emitter junction configured to emit a laser beam; and a battery source;

via the laser control circuit, providing current from the battery source to the laser diode to cause each of the at least two emitter junctions to concurrently emit a laser beam, the at least two concurrently emitted laser beams at least partially combining or interacting to form a collective beam having a fast-axis beam profile shape that defines multiple spaced-apart intensity peaks corresponding to the multiple emitter junctions of the MQW laser diode;

passing the collective beam through a downstream optical element that optically influences collective beam such that, downstream of the downstream optical element, the fast-axis beam profile shape of the collective beam changes from a first profile shape defining multiple spaced-apart intensity peaks to a second profile shape defining a single intensity peak; and delivering the output collective beam with the second profile shape defining a single intensity peak to the target area of tissue to provide a contiguous treatment spot on the tissue for providing a dermatological treatment.

29. A dermatological treatment device, comprising:

a device body configured to be handheld;

an application end configured to be in contact with or proximate the skin during a treatment session;

a laser control circuit housed in the device body and configured to generate laser radiation for delivery to a target area of tissue, the circuit comprising:

exactly one multi-quantum well (MQW) laser diode including a monolithic stack of layers formed on a substrate, the monolithic stack of layers including a multiple-emitter region defining at least two emitter junctions connected in electrical series and aligned along a fast-axis direction of the emitter junctions, each emitter junction configured to emit a laser beam; and a battery source that provides current to the laser diode such that each of the at least two emitter junctions concurrently emits a laser beam, the at least two concurrently emitted laser beams at least partially combining or interacting to form a single collective beam having a beam profile including a fast-axis beam profile shape that defines multiple spaced-apart intensity peaks corresponding to the multiple emitter junctions of the MQW laser diode; and a downstream optical element arranged downstream of the laser diode and proximate the application end of the device, wherein the downstream optical element is configured to:

receive the single collective beam, the fast-axis beam profile shape of the single received collective beam defining multiple spaced-apart intensity peaks;

output the single collective beam, the fast-axis beam profile shape of the single output collective beam defining multiple spaced-apart intensity peaks; and optically influence the beam profile of the single collective beam such that, downstream of the downstream optical element, the fast-axis beam profile shape of the single output collective beam changes from a first profile shape defining multiple spaced-apart intensity peaks to a second profile shape defining a single intensity peak;

wherein the device is configured for delivering the single output collective beam with the second profile shape defining a single intensity peak to the target area of tissue to generate exactly one treatment spot on the tissue at a time.

* * * * *